United States Patent
Ortiz et al.

(10) Patent No.: US 7,328,828 B2
(45) Date of Patent: Feb. 12, 2008

(54) LOCKOUT MECHANISMS AND SURGICAL INSTRUMENTS INCLUDING SAME

(75) Inventors: Mark S. Ortiz, Milford, OH (US); Chad Paul Boudreaux, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/266,961

(22) Filed: Nov. 4, 2005

(65) Prior Publication Data

US 2007/0102475 A1    May 10, 2007

(51) Int. Cl.
*A61B 17/04*    (2006.01)

(52) U.S. Cl. .............. 227/175.2; 227/19; 227/181.1

(58) Field of Classification Search ............ 227/175.2, 227/19, 175.4, 181.1
See application file for complete search history.

(56) References Cited

U.S. PATENT DOCUMENTS

| | | | |
|---|---|---|---|
| 2,037,727 A | 4/1936 | Chapelle | |
| 3,269,630 A | 8/1966 | Fleischer | |
| 3,734,207 A | 5/1973 | Fishbein | |
| 3,894,174 A | 7/1975 | Cartun | |
| 3,940,844 A | 3/1976 | Colby et al. | |
| 4,415,112 A | 11/1983 | Green | |
| 4,475,679 A | 10/1984 | Fleury, Jr. | |
| 4,520,817 A | 6/1985 | Green | |
| 4,526,174 A | 7/1985 | Froehlich | |
| 4,605,001 A * | 8/1986 | Rothfuss et al. | 227/178.1 |
| 4,606,343 A | 8/1986 | Conta et al. | |
| 4,608,981 A * | 9/1986 | Rothfuss et al. | 227/180.1 |
| 4,709,120 A | 11/1987 | Pearson | |
| 4,869,415 A * | 9/1989 | Fox | 227/19 |
| 4,892,244 A | 1/1990 | Fox et al. | |

(Continued)

FOREIGN PATENT DOCUMENTS

DE    9412228 U    9/1994

(Continued)

OTHER PUBLICATIONS

U.S. Appl. No. 11/061,908, filed Feb. 18, 2005, Wales et al.

(Continued)

*Primary Examiner*—Brian D. Nash
(74) *Attorney, Agent, or Firm*—Kirkpatrick & Lockhart Preston Gates Ellis LLP

(57) ABSTRACT

A surgical instrument is disclosed. The surgical instrument includes a handle portion, a channel, an anvil, and staple cartridge, a wedge member, a reciprocating firing device, and a lockout arm. The handle portion is operably configured to produce a firing motion and is coupled to the channel portion. The staple cartridge is engaged by the channel and includes a plurality of staple drivers to cam the staples toward the anvil, which is pivotally attached to the channel. The wedge member is proximal to and longitudinally aligned with the staple drivers, and the reciprocating firing device is responsive to the firing motion to progressively drive the wedge member from an unfired to a fired position. The lockout arm is pivotally attached to the channel and operably configured to pivot between a locked position and an unlocked position with respect to the firing device based upon a position of the wedge member.

8 Claims, 16 Drawing Sheets

U.S. PATENT DOCUMENTS

| | | | |
|---|---|---|---|
| 4,941,623 A | 7/1990 | Pruitt | |
| 4,955,959 A | 9/1990 | Tompkins et al. | |
| 4,978,049 A | 12/1990 | Green | |
| 5,027,834 A | 7/1991 | Pruitt | |
| 5,031,814 A | 7/1991 | Tompkins et al. | |
| 5,040,715 A | 8/1991 | Green et al. | |
| 5,065,929 A * | 11/1991 | Schulze et al. | 227/19 |
| 5,080,556 A | 1/1992 | Carreno | |
| 5,104,025 A | 4/1992 | Main et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,156,315 A | 10/1992 | Green et al. | |
| 5,200,280 A | 4/1993 | Karasa | |
| 5,207,697 A | 5/1993 | Carusillo et al. | |
| 5,211,649 A | 5/1993 | Kohler et al. | |
| 5,246,156 A | 9/1993 | Rothfuss et al. | |
| 5,253,793 A | 10/1993 | Green et al. | |
| RE34,519 E | 1/1994 | Fox et al. | |
| 5,275,323 A | 1/1994 | Schulze et al. | |
| 5,307,976 A | 5/1994 | Olson et al. | |
| 5,309,927 A | 5/1994 | Welch | |
| 5,318,221 A | 6/1994 | Green et al. | |
| 5,332,142 A * | 7/1994 | Robinson et al. | 227/175.2 |
| 5,350,400 A | 9/1994 | Esposito et al. | |
| 5,379,933 A | 1/1995 | Green et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,397,046 A | 3/1995 | Savage et al. | |
| 5,403,312 A | 4/1995 | Yates et al. | |
| 5,413,267 A | 5/1995 | Solyntjes et al. | |
| 5,413,268 A | 5/1995 | Green et al. | |
| 5,415,335 A | 5/1995 | Knodell, Jr. | |
| 5,425,745 A | 6/1995 | Green et al. | |
| 5,431,322 A | 7/1995 | Green et al. | |
| 5,433,721 A | 7/1995 | Hooven et al. | |
| 5,445,304 A | 8/1995 | Plyley et al. | |
| 5,456,401 A | 10/1995 | Green et al. | |
| 5,462,215 A | 10/1995 | Viola et al. | |
| 5,465,895 A | 11/1995 | Knodel et al. | |
| 5,465,896 A | 11/1995 | Allen et al. | |
| 5,470,006 A | 11/1995 | Rodak | |
| 5,472,132 A | 12/1995 | Savage et al. | |
| 5,474,566 A | 12/1995 | Alesi et al. | |
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,503,320 A | 4/1996 | Webster et al. | |
| 5,503,638 A | 4/1996 | Cooper et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,549,628 A | 8/1996 | Cooper et al. | |
| 5,553,675 A | 9/1996 | Pitzen et al. | |
| 5,554,169 A | 9/1996 | Green et al. | |
| 5,562,239 A | 10/1996 | Boiarski et al. | |
| 5,562,241 A | 10/1996 | Knodel et al. | |
| 5,574,431 A | 11/1996 | McKeown et al. | |
| 5,575,803 A | 11/1996 | Cooper et al. | |
| 5,582,611 A | 12/1996 | Tsuruta et al. | |
| 5,584,425 A | 12/1996 | Savage et al. | |
| 5,586,711 A | 12/1996 | Plyley et al. | |
| 5,628,446 A | 5/1997 | Geiste et al. | |
| 5,632,432 A | 5/1997 | Schulze et al. | |
| 5,636,779 A | 6/1997 | Palmer | |
| 5,651,491 A | 7/1997 | Heaton et al. | |
| 5,653,374 A | 8/1997 | Young et al. | |
| 5,662,258 A | 9/1997 | Knodel et al. | |
| 5,667,517 A | 9/1997 | Hooven | |
| 5,673,840 A | 10/1997 | Schulze et al. | |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,688,270 A | 11/1997 | Yates et al. | |
| 5,692,668 A | 12/1997 | Schulze et al. | |
| 5,693,042 A | 12/1997 | Boiarski et al. | |
| 5,702,408 A | 12/1997 | Wales et al. | |
| 5,704,534 A | 1/1998 | Huitema et al. | |
| 5,706,998 A | 1/1998 | Plyley et al. | |
| 5,709,680 A | 1/1998 | Yates et al. | |
| 5,713,505 A | 2/1998 | Huitema | |
| 5,715,988 A | 2/1998 | Palmer | |
| 5,718,359 A | 2/1998 | Palmer et al. | |
| 5,735,445 A | 4/1998 | Vidal et al. | |
| 5,747,953 A | 5/1998 | Philipp | |
| 5,752,644 A * | 5/1998 | Bolanos et al. | 227/180.1 |
| 5,762,256 A | 6/1998 | Mastri et al. | |
| 5,779,130 A | 7/1998 | Alesi et al. | |
| 5,782,396 A | 7/1998 | Mastri et al. | |
| 5,782,397 A | 7/1998 | Koukline | |
| 5,796,188 A | 8/1998 | Bays | |
| 5,797,537 A | 8/1998 | Oberlin et al. | |
| 5,797,538 A | 8/1998 | Heaton et al. | |
| 5,807,393 A | 9/1998 | Williamson, IV et al. | |
| 5,817,093 A | 10/1998 | Williamson, IV et al. | |
| 5,823,066 A | 10/1998 | Huitema et al. | |
| 5,826,776 A | 10/1998 | Schulze et al. | |
| 5,833,690 A | 11/1998 | Yates et al. | |
| 5,843,132 A | 12/1998 | Ilvento | |
| 5,865,361 A * | 2/1999 | Milliman et al. | 227/176.1 |
| 5,871,135 A | 2/1999 | Williamson, IV et al. | |
| 5,878,938 A | 3/1999 | Bittner et al. | |
| 5,893,506 A | 4/1999 | Powell | |
| 5,894,979 A | 4/1999 | Powell | |
| 5,911,353 A | 6/1999 | Bolanos et al. | |
| 5,918,791 A | 7/1999 | Sorrentino et al. | |
| 5,954,259 A | 9/1999 | Viola et al. | |
| 5,988,479 A | 11/1999 | Palmer | |
| 6,010,054 A | 1/2000 | Johnson et al. | |
| 6,017,356 A | 1/2000 | Frederick et al. | |
| 6,022,352 A | 2/2000 | Vandewalle | |
| 6,024,741 A | 2/2000 | Williamson, IV et al. | |
| 6,024,748 A * | 2/2000 | Manzo et al. | 606/153 |
| 6,032,849 A | 3/2000 | Mastri et al. | |
| 6,079,606 A | 6/2000 | Milliman et al. | |
| 6,083,234 A | 7/2000 | Nicholas et al. | |
| 6,109,500 A | 8/2000 | Alli et al. | |
| H1904 H | 10/2000 | Yates et al. | |
| 6,126,670 A | 10/2000 | Walker et al. | |
| 6,131,789 A | 10/2000 | Schulze et al. | |
| 6,155,473 A | 12/2000 | Tompkins et al. | |
| 6,156,056 A | 12/2000 | Kearns et al. | |
| 6,202,914 B1 | 3/2001 | Geiste et al. | |
| 6,223,835 B1 | 5/2001 | Habedank et al. | |
| 6,241,139 B1 | 6/2001 | Milliman et al. | |
| 6,250,532 B1 | 6/2001 | Green et al. | |
| 6,264,087 B1 | 7/2001 | Whitman | |
| 6,273,897 B1 | 8/2001 | Dalessandro et al. | |
| 6,315,184 B1 | 11/2001 | Whitman | |
| 6,320,123 B1 | 11/2001 | Reimers | |
| 6,325,810 B1 | 12/2001 | Hamilton et al. | |
| 6,330,965 B1 | 12/2001 | Milliman et al. | |
| 6,358,224 B1 | 3/2002 | Tims et al. | |
| 6,416,486 B1 | 7/2002 | Wampler | |

| | | |
|---|---|---|
| 6,443,973 B1 | 9/2002 | Whitman |
| 6,488,197 B1 | 12/2002 | Whitman |
| 6,491,201 B1 | 12/2002 | Whitman |
| 6,503,257 B2 | 1/2003 | Grant et al. |
| 6,511,468 B1 | 1/2003 | Cragg et al. |
| 6,522,101 B2 | 2/2003 | Malackowski |
| 6,592,597 B2 | 7/2003 | Grant et al. |
| 6,602,252 B2 | 8/2003 | Mollenauer |
| 6,619,529 B2 | 9/2003 | Green et al. |
| 6,620,166 B1 | 9/2003 | Wenstrom, Jr. et al. |
| 6,629,988 B2 | 10/2003 | Weadock |
| 6,644,532 B2 | 11/2003 | Green et al. |
| 6,656,193 B2 | 12/2003 | Grant et al. |
| 6,669,073 B2 | 12/2003 | Milliman et al. |
| 6,681,979 B2 | 1/2004 | Whitman |
| 6,695,199 B2 | 2/2004 | Whitman |
| 6,716,233 B1 | 4/2004 | Whitman |
| 6,755,338 B2 | 6/2004 | Hahnen et al. |
| 6,773,438 B1 | 8/2004 | Knodel et al. |
| 6,786,382 B1 | 9/2004 | Hoffman |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,814,741 B2 | 11/2004 | Bowman et al. |
| 6,821,273 B2 | 11/2004 | Mollenauer |
| 6,828,902 B2 | 12/2004 | Casden |
| 6,830,174 B2 | 12/2004 | Hillstead et al. |
| 6,835,199 B2 | 12/2004 | McGuckin, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 | 6/2005 | Swayze et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 7,032,798 B2 | 4/2006 | Whitman et al. |
| 7,044,353 B2 * | 5/2006 | Mastri et al. ............ 227/176.1 |
| 7,048,687 B1 | 5/2006 | Reuss et al. |
| 7,055,730 B2 * | 6/2006 | Ehrenfels et al. ........ 227/175.4 |
| 7,055,731 B2 | 6/2006 | Shelton, IV et al. |
| 7,066,944 B2 | 6/2006 | Laufer et al. |
| 7,077,856 B2 | 7/2006 | Whitman |
| 7,083,075 B2 | 8/2006 | Swayze et al. |
| 7,090,684 B2 | 8/2006 | McGuckin, Jr. et al. |
| 7,098,794 B2 | 8/2006 | Lindsay et al. |
| 7,111,769 B2 * | 9/2006 | Wales et al. ............. 227/178.1 |
| 7,140,527 B2 * | 11/2006 | Ehrenfels et al. ........ 227/175.1 |
| 2002/0117533 A1 | 8/2002 | Milliman et al. |
| 2003/0105478 A1 | 6/2003 | Whitman et al. |
| 2003/0130677 A1 | 7/2003 | Whitman et al. |
| 2003/0216778 A1 | 11/2003 | Weadock |
| 2004/0007608 A1 | 1/2004 | Ehrenfels et al. |
| 2004/0028502 A1 | 2/2004 | Cummins |
| 2004/0094597 A1 | 5/2004 | Whitman et al. |
| 2004/0094598 A1 | 5/2004 | Geiste et al. |
| 2004/0097987 A1 | 5/2004 | Pugsley et al. |
| 2004/0111081 A1 | 6/2004 | Whitman et al. |
| 2004/0122471 A1 | 6/2004 | Toby et al. |
| 2004/0167572 A1 | 8/2004 | Roth et al. |
| 2004/0222268 A1 | 11/2004 | Bilotti et al. |
| 2004/0232195 A1 | 11/2004 | Shelton, IV et al. |
| 2004/0232196 A1 | 11/2004 | Shelton, IV et al. |
| 2004/0232199 A1 | 11/2004 | Shelton, IV et al. |
| 2004/0232200 A1 | 11/2004 | Shelton, IV et al. |
| 2004/0243151 A1 | 12/2004 | Demmy et al. |
| 2004/0243176 A1 | 12/2004 | Hahnen et al. |
| 2005/0006434 A1 | 1/2005 | Wales et al. |
| 2005/0021026 A1 | 1/2005 | Baily |
| 2005/0023324 A1 | 2/2005 | Doll et al. |
| 2005/0070958 A1 | 3/2005 | Swayze et al. |
| 2005/0072827 A1 | 4/2005 | Mollenauer |
| 2005/0107824 A1 | 5/2005 | Hillstead et al. |
| 2005/0119669 A1 | 6/2005 | Demmy |
| 2005/0131390 A1 | 6/2005 | Heinrich et al. |
| 2005/0143759 A1 | 6/2005 | Kelly |
| 2005/0165415 A1 | 7/2005 | Wales |
| 2005/0173490 A1 | 8/2005 | Shelton, IV |
| 2005/0187576 A1 | 8/2005 | Whitman et al. |
| 2005/0189397 A1 | 9/2005 | Jankowski |
| 2005/0203550 A1 | 9/2005 | Laufer et al. |
| 2005/0216055 A1 | 9/2005 | Scirica et al. |
| 2005/0230453 A1 | 10/2005 | Viola |
| 2005/0263562 A1 | 12/2005 | Shelton, IV et al. |
| 2006/0011699 A1 | 1/2006 | Olson et al. |
| 2006/0025812 A1 | 2/2006 | Shelton, IV |
| 2006/0025813 A1 | 2/2006 | Shelton et al. |
| 2006/0025816 A1 | 2/2006 | Shelton |
| 2006/0087442 A1 | 4/2006 | Smith et al. |
| 2006/0100643 A1 | 5/2006 | Laufer et al. |
| 2006/0122636 A1 | 6/2006 | Bailley et al. |
| 2006/0142772 A1 | 6/2006 | Ralph et al. |
| 2006/0151567 A1 | 7/2006 | Roy |
| 2007/0034668 A1 | 2/2007 | Holsten et al. |
| 2007/0045379 A1 | 3/2007 | Shelton |

FOREIGN PATENT DOCUMENTS

| | | |
|---|---|---|
| DE | 69328576 T2 | 1/2001 |
| EP | 0122046 A1 | 10/1984 |
| EP | 0839349 A2 | 2/1994 |
| EP | 0630612 A1 | 12/1994 |
| EP | 0634144 A1 | 1/1995 |
| EP | 0879367 A2 | 11/1995 |
| EP | 0685204 A1 | 12/1995 |
| EP | 0699418 A1 | 3/1996 |
| EP | 0705571 A1 | 4/1996 |
| EP | 0667119 B1 | 7/1996 |
| EP | 0552423 B1 | 1/1998 |
| EP | 0760230 B1 | 2/1999 |
| EP | 0552050 B1 | 5/2000 |
| EP | 1256318 B1 | 5/2001 |
| EP | 1238634 A2 | 9/2002 |
| EP | 0656188 B1 | 1/2003 |
| EP | 0705570 B1 | 4/2004 |
| EP | 1086713 B1 | 5/2004 |
| EP | 1426012 A1 | 6/2004 |
| EP | 1477119 A1 | 11/2004 |
| EP | 1520525 A1 | 4/2005 |
| EP | 1550408 A1 | 7/2005 |
| EP | 1064883 B1 | 8/2005 |
| EP | 1621141 A2 | 2/2006 |
| EP | 1045672 B1 | 8/2006 |
| EP | 1617768 B1 | 8/2006 |
| EP | 1129665 B1 | 11/2006 |
| EP | 1256317 B1 | 12/2006 |
| EP | 1479346 B1 | 1/2007 |
| JP | 6007357 A | 1/1994 |
| JP | 7051273 A | 2/1995 |
| JP | 8033641 A | 2/1996 |
| JP | 8229050 A | 9/1996 |
| JP | 2001286477 A | 10/2001 |
| JP | 2002369820 A | 12/2002 |
| JP | 2005103293 A | 4/2005 |
| WO | WO 96/35464 A1 | 11/1996 |
| WO | WO 99/15086 A1 | 4/1999 |
| WO | WO 99/34744 A1 | 7/1999 |
| WO | WO 00/72762 A1 | 12/2000 |
| WO | WO 00/72765 A1 | 12/2000 |
| WO | WO 01/05702 A1 | 1/2001 |
| WO | WO 01/010482 A1 | 2/2001 |
| WO | WO 01/62158 A2 | 8/2001 |
| WO | WO 01/62162 A1 | 8/2001 |

| | | |
|---|---|---|
| WO | WO 01/62164 A2 | 8/2001 |
| WO | WO 01/91646 A1 | 12/2001 |
| WO | WO 0230297 A2 * | 4/2002 |
| WO | WO 02/043571 A2 | 6/2002 |
| WO | WO 02/067785 A2 | 9/2002 |
| WO | WO 03/000138 A2 | 1/2003 |
| WO | WO 03/001329 A2 | 1/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/090630 A2 | 11/2003 |
| WO | WO 03/094747 A1 | 11/2003 |
| WO | WO 04/032763 A2 | 4/2004 |
| WO | WO 2005/027983 A2 | 3/2005 |

OTHER PUBLICATIONS

European Search Report, Application No. 06255683.2, dated Mar. 5, 2007 (5 pages).

* cited by examiner

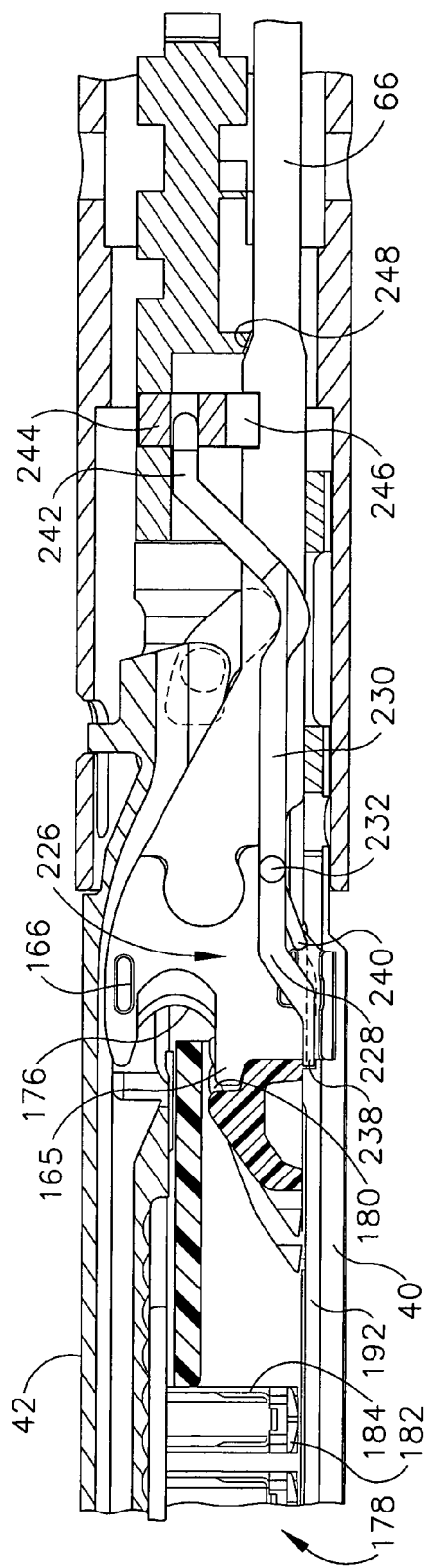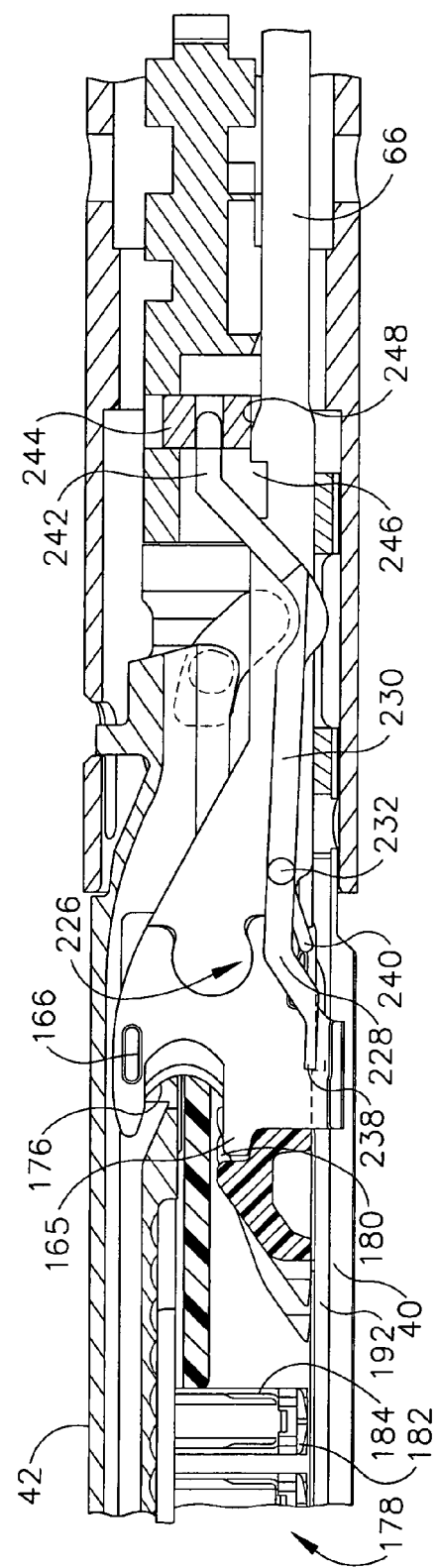
FIG. 6
FIG. 7

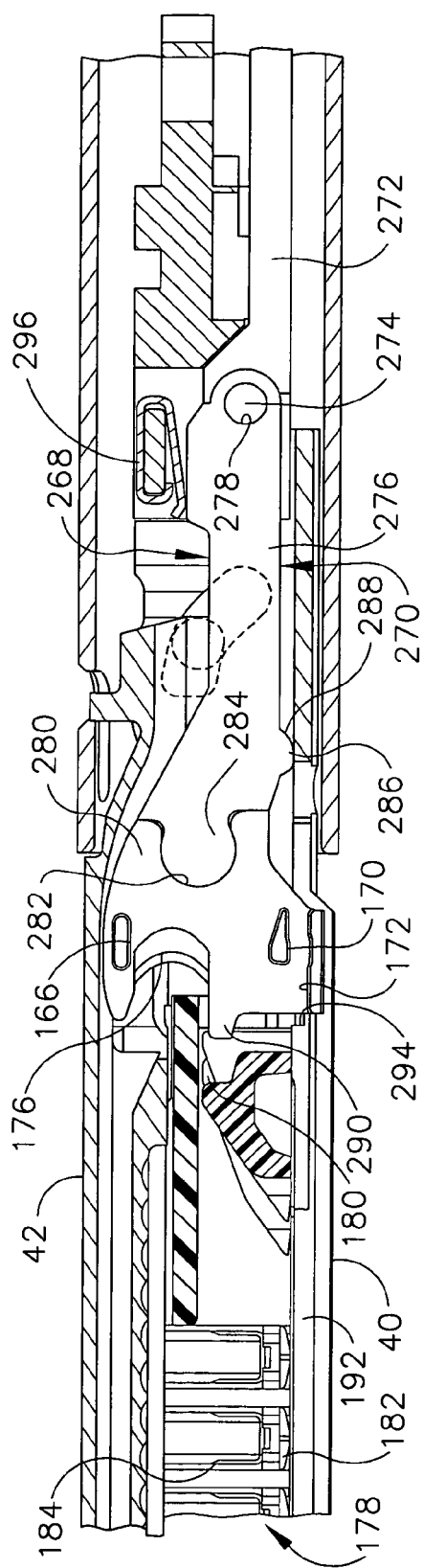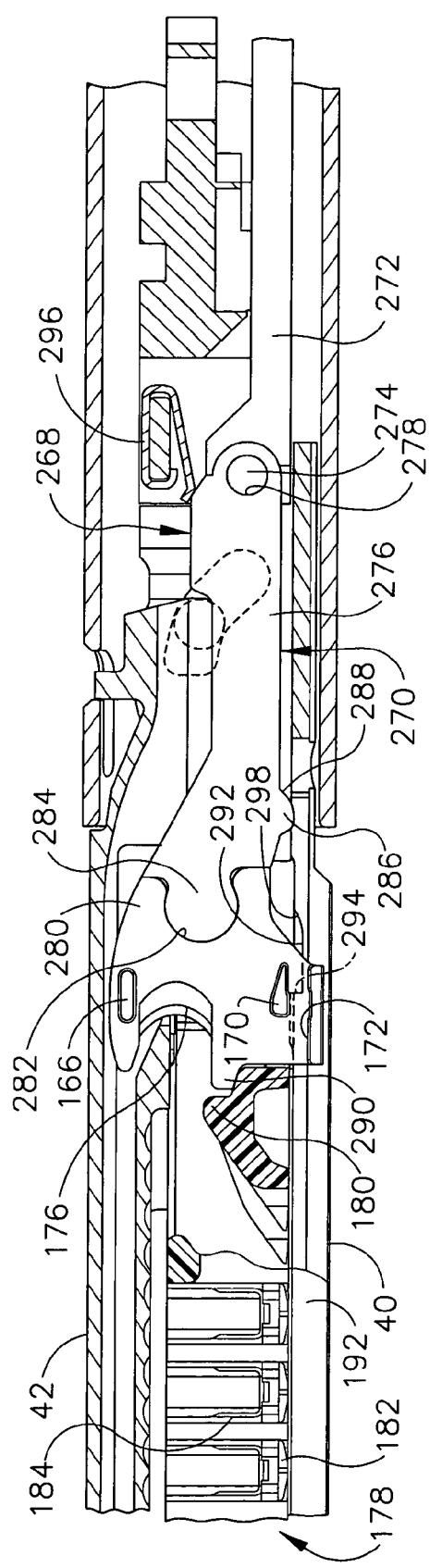

LOCKOUT MECHANISMS AND SURGICAL INSTRUMENTS INCLUDING SAME

FIELD OF THE INVENTION

The disclosed invention relates generally and in various embodiments to surgical stapling and cutting instruments structured and configured for applying lines of staples from a reusable staple cartridge into tissue while cutting the tissue between the applied staple lines. More particularly the disclosed invention relates to locking mechanisms for use in articulating surgical stapling and cutting instruments that prevent cutting of the tissue when the staple cartridge is spent or otherwise not present in an unfired position.

BACKGROUND OF THE INVENTION

Surgical stapling and cutting instruments have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler. Firing places all of the staples into the tissue and advances a knife to sever the tissue. The simultaneous severing and stapling avoids complications that may arise when performing such actions sequentially with different surgical tools that respectively only sever or staple.

It is often advantageous to build an end effector for the surgical stapler that is reusable. For instance, one patient may need a series of severing and stapling operations. Replacing an entire end effector for each operation tends to be economically inefficient. This is especially true if the end effector is built for strength and reliability over repeated operations. To that end, staple cartridges are fitted into the end effector prior to each operation of the surgical stapler. Thus, a much smaller amount of the surgical staples is discarded after each use.

While the staple cartridge provides numerous advantages, it is desirable to prevent inadvertent firing of the instrument when an unfired staple cartridge is not present. Otherwise, the severing of tissue may occur without the staples to minimize bleeding. It is particularly desirable that preventing such inadvertent firing be accomplished in a reliable way that is not subject to an intervening malfunction. Moreover, for ease of manufacturing and assembly, it is further desirable that the lockout features be accomplished with a minimum number of components.

Lockout mechanisms based upon vertical movement of the knife are known and particularly well-suited for non-articulating endocutter designs in which the end effector is located at the end of a generally rigid shaft. The shaft enables insertion to a desired depth and rotation about the longitudinal axis of the shaft, thereby enabling the end effector to be positioned to a degree. A U.S. Pat. No. 5,878,938 to Bittner et al. discloses a locking mechanism, or lockout, that uses a leaf spring to automatically lift a knife of the cartridge after a firing operation, thus locking the instrument so that subsequent firing operations are prevented. U.S. Pat. No. 5,673,842, also to Bittner et al., teaches a locking mechanism using an elongated member that automatically rotates from a first position to a second position as the instrument is fired. With the locking arm in the second position, the knife is free to translate upwardly and lock the instrument.

Such lockout mechanisms may be less suited for use in articulating surgical stapling and cutting instrument designs in which the end effector is located at the end of a shaft incorporating an articulating mechanism. A U.S. Pat. No. 6,786,382 to Hoffman discloses a surgical stapling and severing instrument incorporating an articulation mechanism for coupling the shaft to the end effector. Firing of the staples and severing of tissue is effected by a flexible firing mechanism extending through the articulation mechanism that is capable of transferring large loads therethrough in both flexed or unflexed states. Despite the greater clinical flexibility generally afforded by articulating instrument designs, the geometry of the firing mechanism and/or the physical forces present while the firing mechanism is in a flexed state may sufficiently restrict its vertical movement such that the above-described lockout mechanisms cannot be effectively employed.

Consequently, a significant need exists for improved lockout mechanisms for use in articulating surgical stapling and severing instruments that prevent inadvertent firing (i.e., severing and stapling) when a staple cartridge is spent or otherwise not present in an unfired position.

BRIEF SUMMARY OF THE INVENTION

This application discloses a surgical instrument comprising a handle portion, a channel, an anvil, and staple cartridge, a wedge member, a reciprocating firing device, and a lockout arm. The handle portion is operably configured to produce a firing motion and is coupled to the channel portion. The staple cartridge is engaged by the channel and includes a plurality of staple drivers and staples. The staple drivers are configured for camming the staples toward the anvil, which is pivotally attached to the channel. The wedge member is proximal to and longitudinally aligned with the staple drivers, and the reciprocating firing device is responsive to the firing motion to progressively drive the wedge member from an unfired to a fired position. The lockout arm is pivotally attached to the channel and operably configured to pivot between a locked position and an unlocked position with respect to the firing device based upon a position of the wedge member.

This application further discloses a surgical instrument comprising a handle portion, a channel, an anvil, and staple cartridge, a wedge member, a reciprocating firing device, and at least one lockout assembly. The handle portion is operably configured to produce a firing motion and is coupled to the channel portion. The staple cartridge is engaged by the channel and includes a plurality of staple drivers and staples. The staple drivers are configured for camming the staples toward the anvil, which is pivotally attached to the channel. The wedge member is proximal to and longitudinally aligned with the staple drivers, and the reciprocating firing device is responsive to the firing motion to progressively drive the wedge member from an unfired to a fired position. Each lockout assembly includes a lockout cartridge moveably disposed within a corresponding recess defined by the channel. The lockout cartridge is configured to move between a locked position and an unlocked position with respect to the firing device based upon a position of the wedge member.

This application further discloses a surgical instrument comprising a handle portion, a channel, an anvil, and staple cartridge, a wedge member, and a reciprocating firing device. The handle portion is operably configured to produce a firing motion and is coupled to the channel portion. The staple cartridge is engaged by the channel and includes a plurality of staple drivers and staples. The staple drivers are configured for camming the staples toward the anvil, which is pivotally attached to the channel. The wedge member is proximal to and longitudinally aligned with the staple drivers, and the reciprocating firing device is responsive to the firing motion to progressively drive the wedge member from an unfired to a fired position. The firing device includes a distal portion, a proximal portion, and pivot means connecting the proximal and distal portions. The distal portion is configured to pivot between a locked position and an unlocked position with respect to the channel based upon a position of the wedge member.

This application further discloses an end effector for use with a surgical instrument, the end effector comprising a channel, a reciprocating firing device, and a lockout arm. The channel is configured for receiving a staple cartridge, and the firing device is responsive to a firing motion produced by the surgical instrument for progressively driving a wedge member of the staple cartridge from an unfired position to a fired position. The lockout arm is pivotally attached to the channel and operably configured to pivot between a locked position and an unlocked position with respect to the firing device based upon a position of the wedge member.

This application further discloses an end effector for use with a surgical instrument, the end effector comprising a channel, a reciprocating firing device, and at least one lockout assembly. The channel is configured for receiving a staple cartridge, and the firing device is responsive to a firing motion produced by the surgical instrument for progressively driving a wedge member of the staple cartridge from an unfired position to a fired position. Each lockout assembly is positioned in the channel and adjacent to a corresponding lateral surface of the firing device and comprises a lockout cartridge moveably disposed within a corresponding recess defined by the channel. The lockout cartridge is configured to move between a locked position and an unlocked position with respect to the firing device based upon a position of the wedge member.

This application further discloses an end effector for use with a surgical instrument, the end effector comprising a channel and a reciprocating firing device. The channel is configured for receiving a staple cartridge, and the firing device is responsive to a firing motion produced by the surgical instrument for progressively driving a wedge member of the staple cartridge from an unfired position to a fired position. The firing device comprises a distal portion, a proximal portion, and pivot means connecting the proximal and distal portions. The distal portion is configured to pivot between a locked position and an unlocked position with respect to the channel based upon a position of the wedge member.

BRIEF DESCRIPTION OF THE FIGURES

FIGS. 6-8 are cross-sectional side views of the end effector of FIGS. 3-4 sequentially shown in a staple cartridge loaded and unfired state in FIG. 6, a staple cartridge being fired state in FIG. 7, and a spent staple cartridge with firing bar retracted state in FIG. 8, according to various embodiments;

FIGS. 16-18 are cross-sectional front views of the end effector of FIG. 14 sequentially shown in a staple cartridge loaded and unfired state in FIG. 16, a staple cartridge being fired state in FIG. 17, and a spent staple cartridge being re-fired state in FIG. 18, according to various embodiments.

DETAILED DESCRIPTION OF THE INVENTION

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Figure 1:
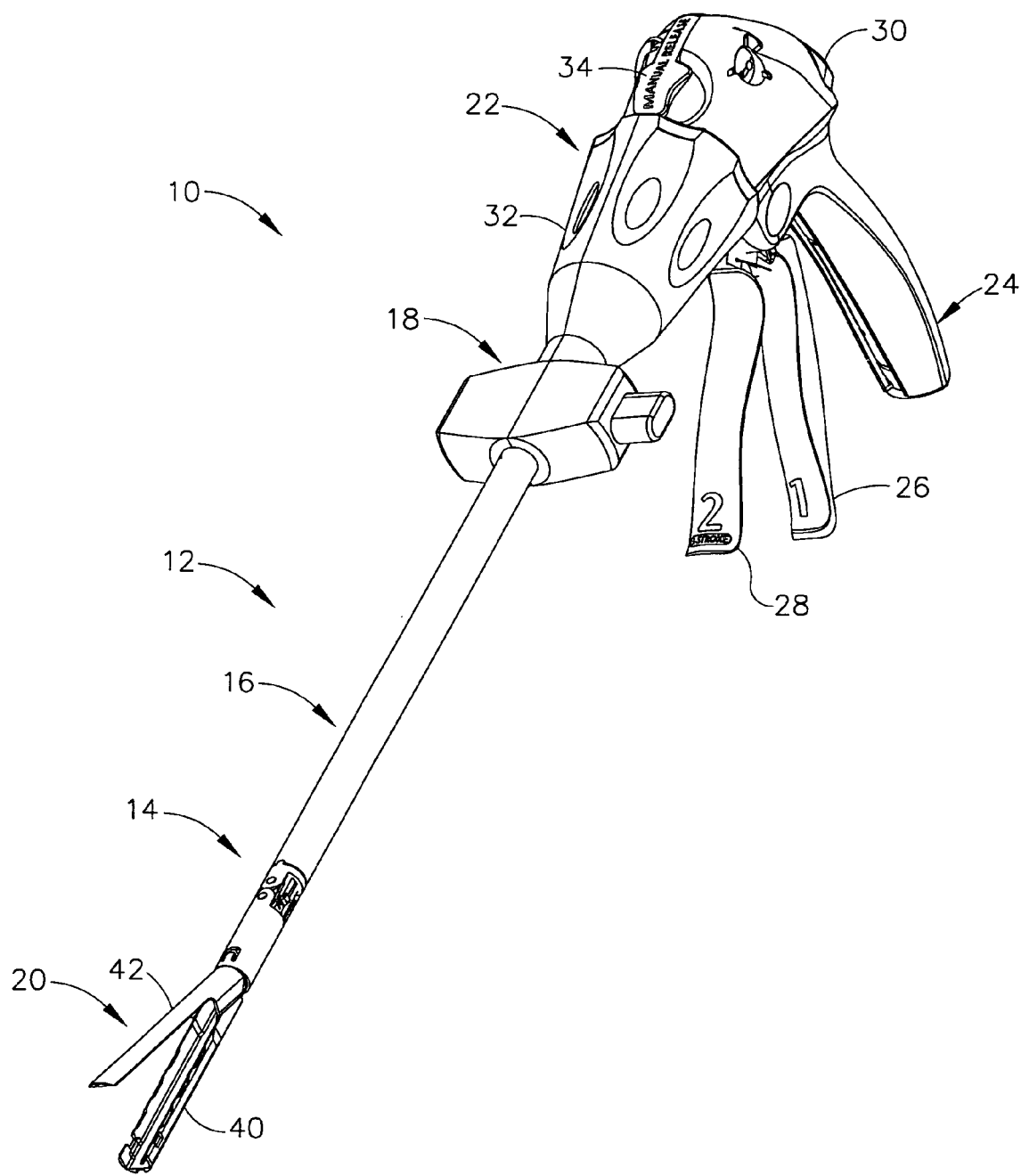
FIG. 1 is a front top perspective view of a surgical stapling and severing instrument shown with an open end effector, or staple applying assembly, and with the staple cartridge removed, according to various embodiments.
Figure 2:
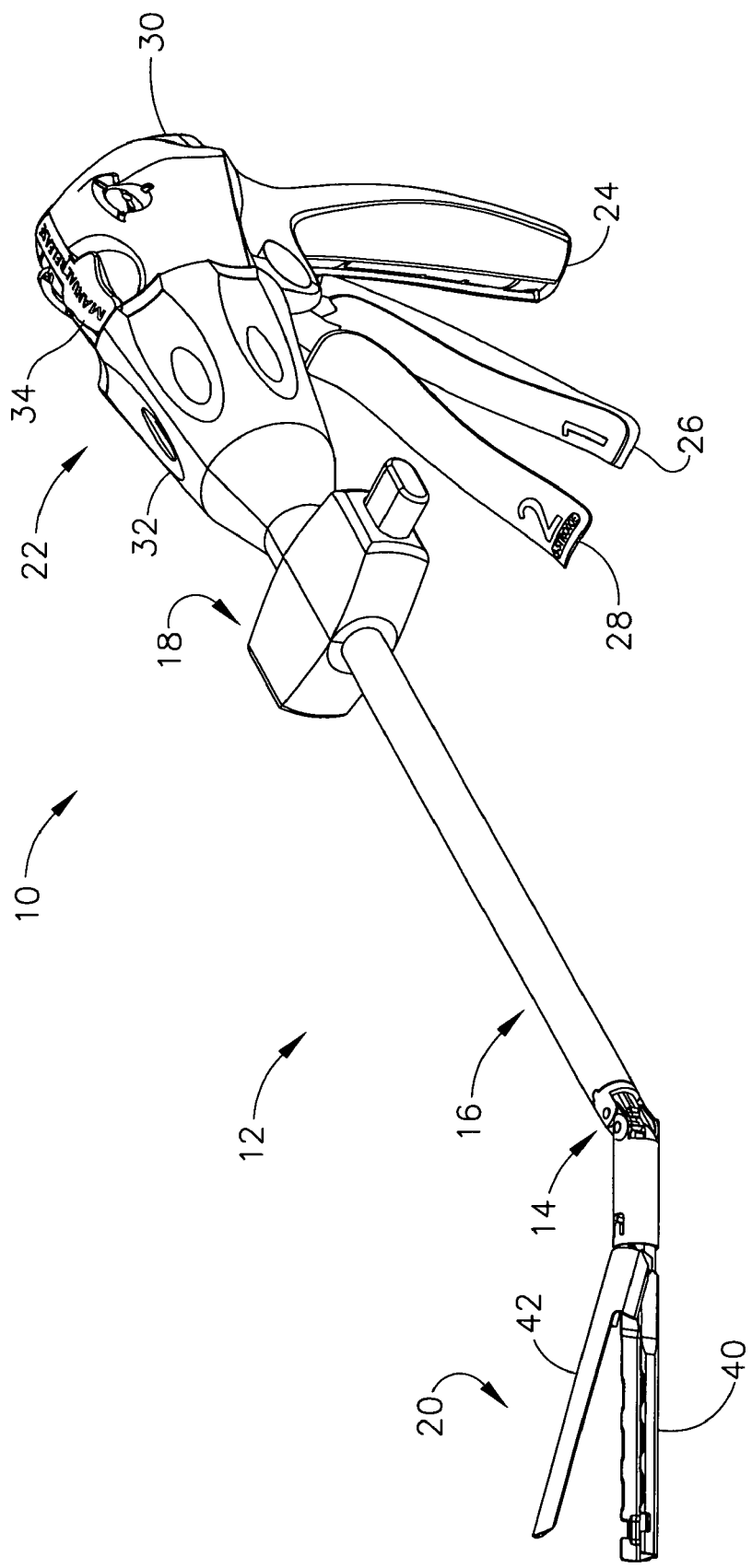
FIG. 2 is a front top perspective view of the surgical stapling and severing instrument of FIG. 1 with an articulation mechanism actuated by a fluidic actuation control, according to various embodiments.

Turning to the Drawings, wherein like numerals denote like components throughout the several views, FIG. 1 depicts a surgical instrument, which in the illustrative versions is more particularly a surgical stapling and severing instrument 10, that is capable of practicing the unique benefits of the present invention. In particular, the surgical stapling and severing instrument 10 is sized for insertion, in a nonarticulated state as depicted in FIG. 1, through a trocar cannula passageway to a surgical site in a patient (not shown) for performing a surgical procedure. Once an implement portion 12 is inserted through a cannula passageway, an articulation mechanism 14 incorporated into a distal portion of an elongate shaft 16 of the implement portion 12 may be remotely articulated, as depicted in FIG. 2, by an articulation control 18. An end effector, depicted in the illustrative version as a staple applying assembly 20, is distally attached to the articulation mechanism 14. Thus, remotely articulating the articulation mechanism 14 thereby articulates the staple applying assembly 20 from a longitudinal axis of the elongate shaft 16. Such an angled position may have advantages in approaching tissue from a desired angle for severing and stapling, approaching tissue otherwise obstructed by other organs and tissue, and/or allowing an endoscope to be positioned behind and aligned with the staple applying assembly 20 for confirming placement.

The surgical and stapling and severing instrument 10 includes a handle portion 22 proximally connected to the implement portion 12 for providing positioning, articulation, closure and firing motions thereto. The handle portion 22 includes a pistol grip 24 toward which a closure trigger 26 is pivotally and proximally drawn by the clinician to cause clamping, or closing, of the staple applying assembly 20. A firing trigger 28 is farther outboard of the closure trigger 26 and is pivotally drawn by the clinician to cause the stapling and severing of clamped tissue clamped in the staple applying assembly 20. Thereafter, a closure release button 30 is depressed to release the clamped closure trigger 26, and thus the severed and stapled ends of the clamped tissue. The handle portion 22 also includes a rotation knob 32 coupled for movement with the elongate shaft 16 to rotate the shaft 16 and the articulated staple applying assembly 20 about the longitudinal axis of the shaft 16. The handle portion 22 also includes a firing retraction handle 34 to assist in retracting a firing mechanism (not depicted in FIGS. 1-2) should binding occur, so that opening of the staple applying assembly 20 may occur thereafter.

It will be appreciated that the terms "proximal" and "distal" are used herein with reference to a clinician gripping a handle of an instrument. Thus, the surgical stapling assembly 20 is distal with respect to the more proximal handle portion 22. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

An illustrative multi-stroke handle portion 22 for the surgical stapling and severing instrument 10 of FIGS. 1-2 is described in greater detail in the co-pending and commonly-owned U.S. patent application entitled "SURGICAL STAPLING INSTRUMENT INCORPORATING A MULTI-STROKE FIRING POSITION INDICATOR AND RETRACTION MECHANISM" to Swayze and Shelton IV, Ser. No. 10/674,026, filed Sep. 29, 2003, the disclosure of which is hereby incorporated by reference in its entirety, with additional features and variation as described herein. While a multi-stroke handle portion 22 advantageously supports applications with high firing forces over a long distance, applications consistent with the present invention may incorporate a single firing stroke, such as described in co-pending and commonly owned U.S. patent application "SURGICAL STAPLING INSTRUMENT HAVING SEPARATE DISTINCT CLOSING AND FIRING SYSTEMS" to Frederick E. Shelton IV, Michael E. Setser, and Brian J. Hemmelgarn, Ser. No. 10/441,632, filed Nov. 25, 2004, the disclosure of which is hereby incorporated by reference in its entirety.

Figure 3:
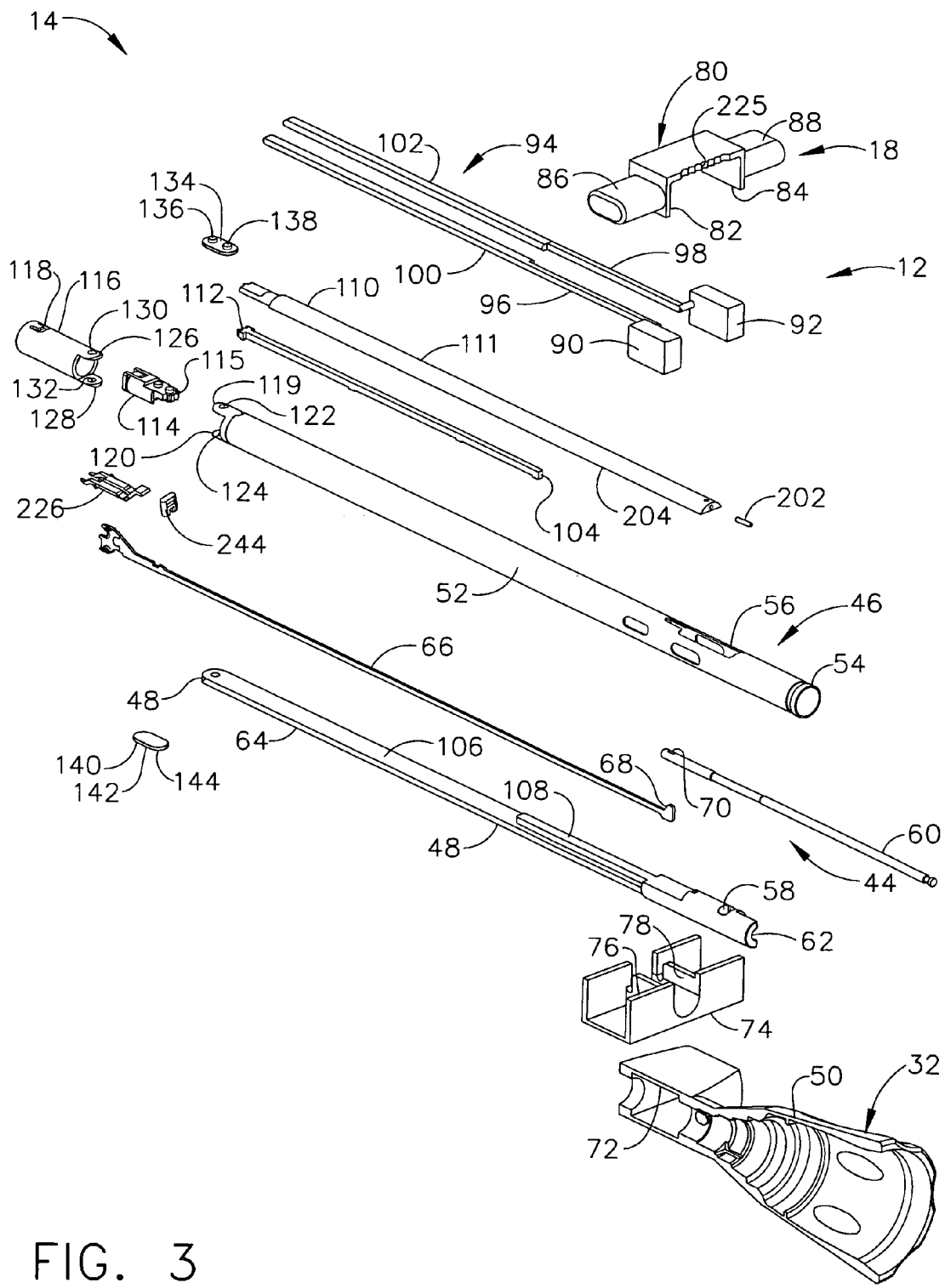
FIG. 3 is a perspective disassembled view of an elongate shaft and articulation mechanism of the surgical stapling and severing instrument of FIG. 1, according to various embodiments.
Figure 4:
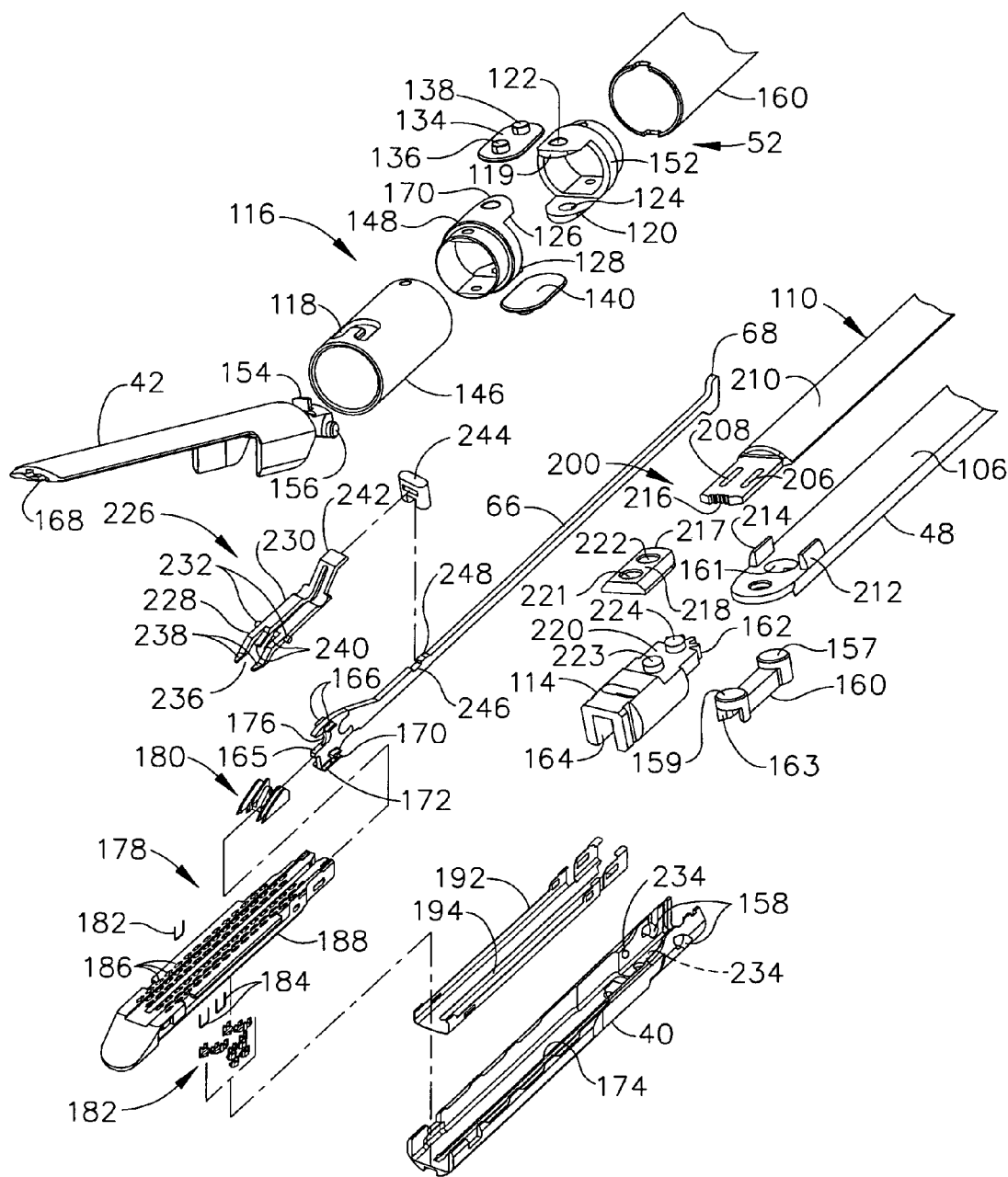
FIG. 4 is a perspective disassembled view of distal portions of an implement portion of the surgical stapling and severing instrument of FIG. 1, including the staple applying assembly and articulation mechanism, according to various embodiments.

In FIGS. 3-4, the implement portion 12 advantageously incorporates the multiple actuation motions of longitudinal rotation, articulation, closure and firing within a small diameter suitable for endoscopic and laparoscopic procedures. The staple applying assembly 20 ("end effector") has a pair of pivotally opposed jaws, depicted as an elongate channel 40 with a pivotally attached anvil 42 (FIGS. 1-2, 4). Closure and clamping of the anvil 42 to the elongate channel 40 is achieved by longitudinally supporting the elongate channel 40 with a frame assembly 44 (FIG. 3) rotatingly attached to the handle portion 22 over which a double pivot closure sleeve assembly 46 longitudinally moves to impart a closing and opening respectively to a distal and proximal motion to the anvil 42, even with the staple applying assembly 20 articulated as in FIG. 2.

With particular reference to FIG. 3, the frame assembly 44 includes a single pivot frame ground 48 whose proximal end is engaged to the rotation knob 32, with a right half shell 50 thereon shown in FIG. 3. It should be appreciated a proximal end of the closure sleeve assembly 46, specifically of a closure straight tube 52, encompasses the proximal end of the frame ground 48, passing further internally to the handle portion 22 to engage closure components (not shown) that longitudinally translate the closure sleeve assembly 46. A circular lip 54 at the proximal end of the closure straight tube 52 provides a rotating engagement to such components. Engaging components of the rotation knob 32 pass through a longitudinal slot 56 on a proximal portion of the straight closure tube 52 to engage an aperture 58 proximally positioned on the frame ground 48. The longitudinal slot 56 is of sufficient length to allow the closure longitudinal translation of the closure sleeve assembly 46 at various rotational angles set by the rotation knob 32 to the closure sleeve assembly 46 and the frame ground 48.

The elongate shaft 16 supports the firing motion by receiving a firing rod 60 that rotatingly engages firing components of the handle portion 22 (not shown). The firing rod 60 enters a proximal opening 62 along the longitudinal centerline of the frame ground 48. The distal portion of the frame ground 48 includes a firing bar slot 64 along its bottom that communicates with the proximal opening 62. A firing bar 66 longitudinally translates in the firing bar slot 64 and includes an upwardly projecting proximal pin 68 that engages a distal end 70 of the firing rod 60.

The elongate shaft 16 supports articulation by incorporating a rectangular reservoir cavity 72, one lateral portion of which is depicted in a distal portion of the rotation knob 32. A bottom compartment 74 that resides within the rectangular reservoir cavity 72 has laterally spaced apart left and right baffles 76, 78. An articulation actuator 80 slides laterally over top of the bottom compartment 74, its downward laterally spaced left and right flanges 82, 84, which are outboard of the baffles 76, 78, each communicating laterally to left and right push buttons 86, 88 that extend outwardly from the respective shell halves of the rotation knob 32. The lateral movement of the articulation actuator 80 draws left and right flanges 82, 84 nearer and farther respectively to the left and right baffles 76, 78, operating against left and right reservoir bladders 90, 92 of a fluidic articulation system 94, each bladder 90, 92 communicating respectively and distally to left and right fluid conduits or passageways 96, 98 that in turn communicate respectively with left and right actuating bladders 100, 102. The latter oppose and laterally pivot a T-bar 104 of the articulation mechanism 14.

The frame assembly 44 constrains these fluidic actuations by including a top and distal recessed table 106 of the frame ground 48 upon which resides the fluid passages 96, 98 and actuating bladders 100, 102. The T-bar 104 also slidingly resides upon the recessed table 106 between the actuating bladders 100, 102. Proximal to the T-Bar 104, a raised barrier rib 108 is aligned thereto, serving to prevent inward expansion of the fluid passages 96, 98. The frame assembly 44 has a rounded top frame cover (spacer) 110 that slides over top of the frame ground 48, preventing vertical expansion of the fluid passages 96, 98 and actuating bladders 100, 102, as well as constraining any vertical movement of the T-bar 104.

A distal end ("rack") 112 of the T-bar 104 engages to pivot a proximally directed gear segment 115 of an articulated distal frame member 114 of the articulation mechanism 14. An articulated closure ring 116 encompasses the articulated frame member 114 and includes a horseshoe aperture 118 that engages the anvil 42. A double pivoting attachment is formed between the closure straight tube 52 and articulating closure ring 116 over the articulating mechanism 14, allowing longitudinal closure motion even when the articulating mechanism 14 is articulated. In particular, top and bottom distally projecting pivot tabs 119, 120 on the closure straight tube 52 having pin holes 122, 124 respectively are longitudinally spaced away from corresponding top and bottom proximally projecting pivot tabs 126, 128 on the articulating closure ring 116 having pin holes 130, 132, respectively. An upper double pivot link 134 has longitudinally spaced upwardly directed distal and aft pins 136, 138 that engage pin holes 130, 122, respectively, and a lower double pivot link 140 has longitudinally spaced downwardly projecting distal and aft pins 142, 144 that engage pin holes 132, 124, respectively.

With particular reference to FIG. 4, the articulating closure ring 116 is shown for enhanced manufacturability to include a short tube 146 attached to an articulating attachment collar 148 that includes the proximally projecting pivot tabs 126, 128. Similarly, the straight closure tube 52 is assembled from a long closure tube 160 that attaches to an aft attachment collar 152 that includes the distally projecting pivot tabs 119, 120. The horseshoe aperture 118 in the short closure tube 146 engages an upwardly projecting anvil feature 154 slightly proximal to lateral pivot pins 156 that engage pivot recesses 158 inside of the elongate channel 40.

The illustrative version of FIG. 4 includes a dog bone link 160 whose proximal pin 157 pivotally attaches to the frame ground 48 in a frame hole 161 and whose distal pin 159 rigidly attaches to a proximal undersurface 162 of the articulating frame member 114, thereby providing pivotal support therebetween. A bottom longitudinal knife slot 163 in the dog bone link 160 guides an articulating portion of the firing bar 66. The articulating frame member 114 also includes a bottom longitudinal slot 164 for guiding a distal portion of the firing bar 66.

With reference to FIG. 4, the firing bar 66 distally terminates in an E-beam 165 that includes upper guide pins 166 that enter an anvil slot 168 in the anvil 42 to verify and assist in maintaining the anvil 42 in a closed state during staple formation and severing. Spacing between the elongate channel 40 and anvil 42 is further maintained by the E-beam 165 by having middle pins 170 slide along the top surface of the elongate channel 40 while a bottom foot 172 opposingly slides along the undersurface of the elongate channel 40, guided by a longitudinal opening 174 in the elongate channel 40. A distally presented cutting surface 176 of the E-beam 165, which is between the upper guide pins 166 and middle pin 170, severs clamped tissue while the E-beam actuates a replaceable staple cartridge 178 by distally moving a wedge sled 180 that causes staple drivers 182 to cam upwardly driving staples 184 out of upwardly open staple holes 186 in a staple cartridge body 188, forming against a staple forming undersurface 190 of the anvil 42. A staple cartridge tray 192 encompasses from the bottom the other components of the staple cartridge 178 to hold them in place. The staple cartridge tray 192 includes a rearwardly open slot 194 that overlies the longitudinal opening 174 in the elongate channel 40. Thus, the middle pins 170 pass inside of the staple cartridge tray 192.

Embodiments of the staple applying assembly 20 are described in greater detail in co-pending and commonly-owned U.S. patent application Ser. No. 10/955,042, "ARTICULATING SURGICAL STAPLING INSTRUMENT INCORPORATING A TWO-PIECE E-BEAM FIRING MECHANISM" to Frederick E. Shelton IV, et al., filed 30 Sep. 2004, the disclosure of which is hereby incorporated by reference in its entirety.

In FIGS. 3-4, an articulation lock mechanism 200 is advantageously incorporated to maintain the staple applying assembly 20 at a desired articulation angle. The articulation lock mechanism 200 reduces loads on the left and right actuating bladders 100, 102. In particular, a compression spring 202 (FIG. 3) is proximally positioned between a proximal end 204 of the articulation locking member 111 and the handle portion 22, biasing the articulation locking member 111 distally. With particular reference to FIG. 4, two parallel slots 206, 208 at a distal end 210 of the articulation locking member 111 receive respectively upwardly projecting guide ribs 212, 214 on the frame ground 48. The guide ribs 212, 214 are longitudinally shorter than the parallel slots 206, 208 allowing a range of relative longitudinal travel. Thereby, selective abutting engagement of a distal frictional surface, depicted as a toothed recess 216 distally projecting from the articulation locking member 111, is engaged to a corresponding locking gear segment 217 in a brake plate 218 received into a top proximal recess 220 of the articulating frame member 114. Distal and proximal holes 221, 222 in the brake plate 218 receive distal and proximal pins 223, 224 that upwardly project from the top proximal recess 220.

Embodiments of the articulation lock mechanism 200 are described in greater detail in co-pending and commonly-owned U.S. patent application Ser. No. 11/061,908, "SURGICAL INSTRUMENT INCORPORATING A FLUID TRANSFER CONTROLLED ARTICULATION MECHA- NISM" to Kenneth S. Wales, et al., filed Feb. 18, 2005, the disclosure of which is hereby incorporated by reference in its entirety.

In FIGS. 3-4, the implement portion 12 advantageously incorporates a lockout arm 226 pivotally attached to the elongate channel 40 and configured to pivot between a locked position and an unlocked position with respect to the firing bar 66 based upon a position of the wedge sled 180. The lockout arm 226 is positioned about the distal end of the firing bar 66 and includes a first end 228 proximately located with respect to the E-beam 165, a second end 230 extending in a proximal direction away from the first end 228 and along the firing bar 66, and pivot means 232 located between the first and second ends 228, 230 for cooperatively engaging corresponding pivot recesses 234 formed in the elongate channel 40. As shown, the pivot means 232 may be implemented as a pair of pivot pins 232 symmetrically formed on opposing sides of the lockout arm 226. The lockout arm 226 defines an open-ended slot 236 passing through the first end 228 and entering a portion of the second end 230, thus enabling the lockout arm 226 to be positioned about the firing bar 66 in a straddle-like configuration so that the firing bar 66 may pass through the lockout arm 226.

The first end 228 of the lockout arm 226 includes a pair of symmetrical tines 238 formed by the passage of the open-ended slot 236 therethrough. When the firing bar 66 is in the retracted position, each tine 238 is adjacently positioned with respect to a corresponding lateral surface of the E-beam 165 and distally extends therealong. As shown, each tine 238 is characterized by downward-sloping portion that transitions into to a tip portion having a flattened, upwardly-facing surface suitable for being depressibly engaged by a bottom surface of the wedge sled 180 when present in the unfired position. The first end 228 further includes biasing means 240 for applying an upwardly-directed force in opposition to the depressible engagement of the tines 238 by the wedge sled 180. Accordingly, when the wedge sled 180 is not present in the unfired position, the biasing means 240 causes the first end 228 of the lockout arm 226 to be pivotally elevated. As shown, the biasing means 240 may be implemented as a pair of downwardly-extending spring fingers 240 positioned between the tines 238 and contacting a bottom portion of the elongate channel 40.

The second end 230 of the lockout arm 226 extends proximally away from the first end 228 along opposing lateral surfaces of the firing bar 66 and transitions into an upwardly-sloping portion having a flattened tip portion 242 positioned above the firing bar 66. As shown, the second end 230 may be suitably contoured so adequate clearance is provided between the lockout arm 226 and the pivot pins 156 of the anvil 42 during operation of the instrument 10. The second end 230 includes a locking pin 244 attached to the tip portion 242 and configured to engage a notch 246 defined by the firing bar 66 when the second end 230 is pivoted in a depressed position with respect thereto. Conversely, the locking pin 244 is disengaged from the notch 246 when the second end 230 is pivoted in an elevated position with respect to the firing bar 66. An inclined contour 248 formed on the firing bar 66 adjacent to the notch 246 and sloping proximally therefrom is provided for guiding the locking pin 244 during reciprocating movement of the firing bar 66, as discussed below in connection with FIGS. 6-8.

The position of the second end 230 of the lockout arm 226 is determined by the engagement of first end 228 by the wedge sled 180. In particular, when the wedge sled 180 is present in the unfired position, the depressible engagement of the tines 238 by the wedge sled 180 causes the second end 230 to be pivotally elevated with respect to the firing bar 66. Accordingly, the locking pin 244 is caused to disengage the notch 246, thus permitting distal movement of the firing bar 66 in response to a firing motion. The depressed engagement of the first end 228 and the resulting pivotal elevation of the second end 230 correspond to the unlocked position of the lockout arm 226. When the wedge sled 180 is not present in the unfired position (e.g., subsequent to a firing operation), the biasing means 240 serves to pivotally elevate the first end 228, causing the second end 230 to be pivotally depressed with respect to the firing bar 66. Accordingly, the locking pin 244 engages the notch 246, thus preventing distal movement of the firing bar 66. The elevation of the first end 228 and the resulting pivotal depression of the second end 230 correspond to the locked position of the lockout arm 226.

Figure 5:
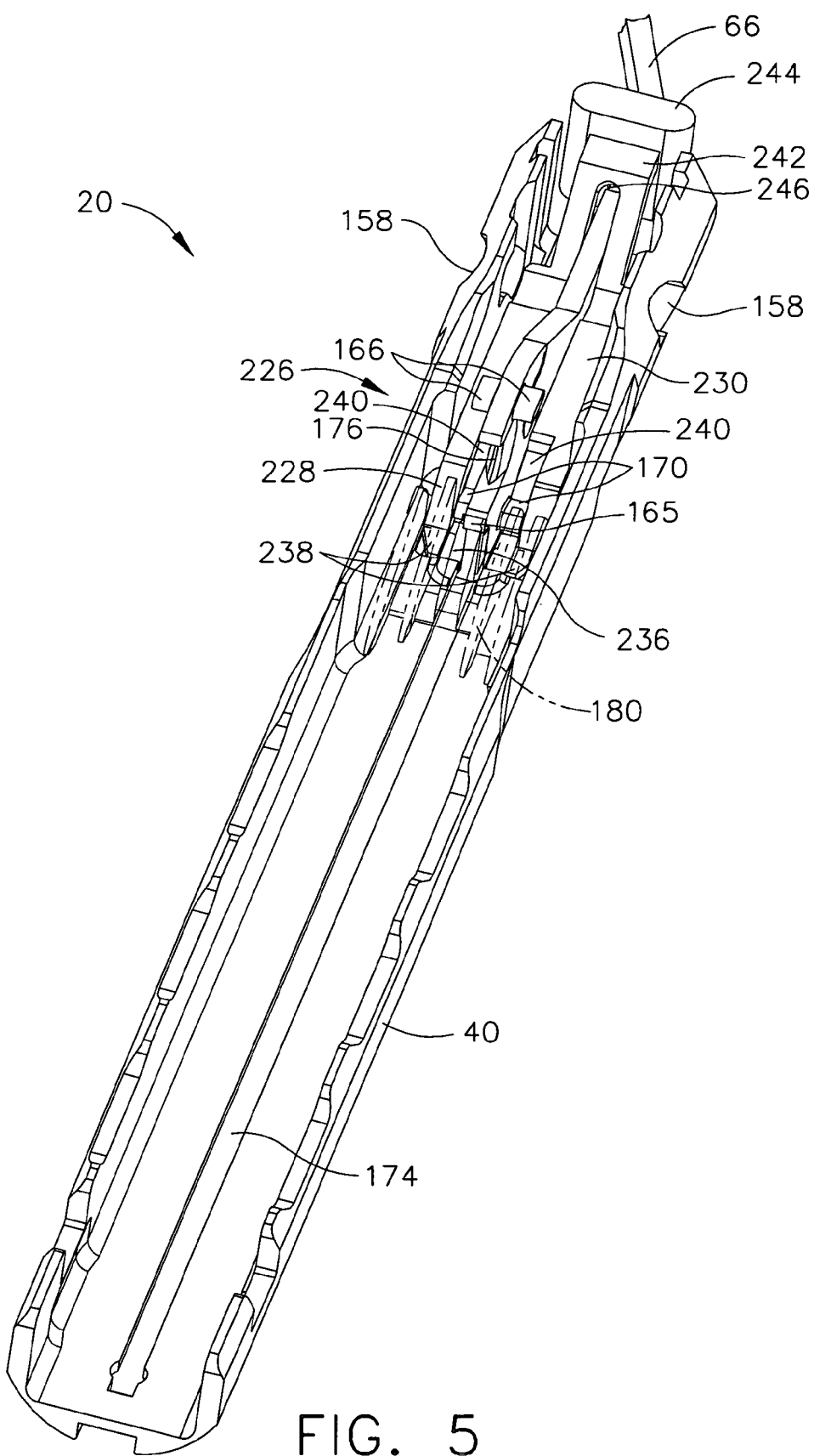
FIG. 5 is a front top perspective view of the end effector at the distal end of the surgical stapling and severing instrument of FIGS. 3-4, with the anvil removed and only the wedge sled of the staple cartridge shown, according to various embodiments.

FIG. 5 is a front top perspective view of the end effector 20 at the distal end of the surgical stapling and severing instrument 10 of FIGS. 3-4, with the anvil 42 removed and only the wedge sled 180 of the staple cartridge 178 shown for the sake of clarity. The firing bar 66 is depicted in a retracted state, with the lockout arm 226 in the unlocked position with respect thereto. The depressed engagement of the tines 238 resulting from the presence of the wedge sled 180 in the unfired position results in pivotal elevation of the second end 230 of the lockout arm 226 with respect to the firing bar 66. Accordingly, as shown in FIG. 5, the locking pin 244 is disengaged from the notch 246, thus enabling distal movement of the firing bar 66. Importantly, because the position of the lockout arm 226 is based only upon the position of the wedge sled 180, operation of the lockout arm 226 is unaffected by flexure of the firing bar 66 resulting from actuation of the articulation mechanism 14.

Figure 8:
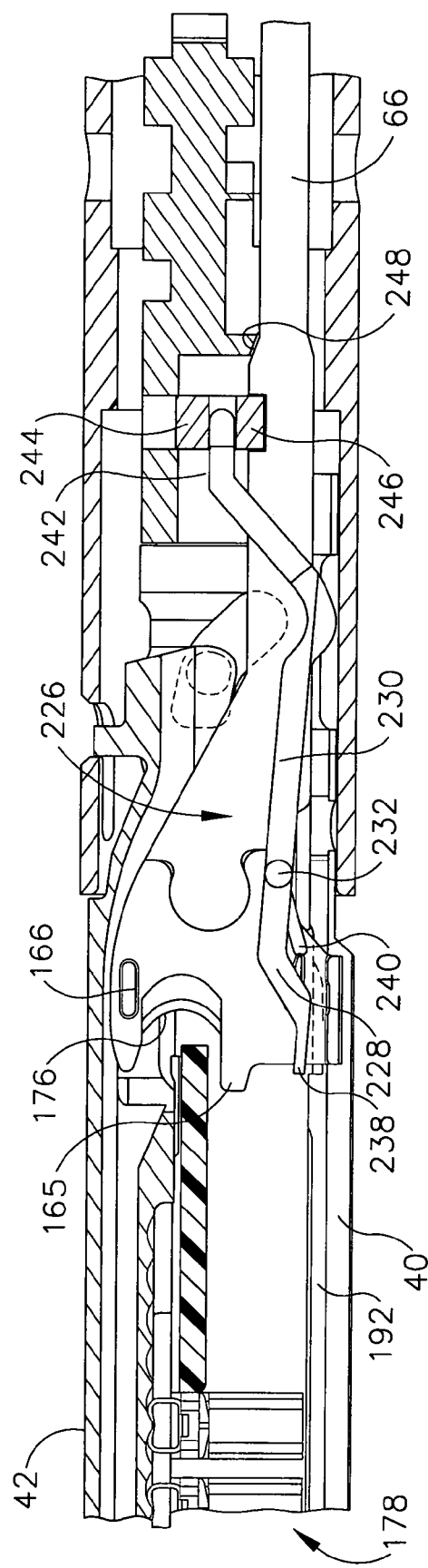

FIGS. 6-8 depict sequential operation of the lockout arm 226 within the end effector 20 of FIGS. 3-4 as the surgical stapling and severing instrument 10 is fired. In FIG. 6, an unfired staple cartridge 178 has been inserted into the elongate channel 40, with the wedge sled 180 depressibly engaging the tines 238 of the lockout arm 226. Accordingly, the lockout arm 226 is in the unlocked position and the locking pin 244 is disengaged from the slot 246 of the firing bar 66.

In FIG. 7, firing of the staple cartridge 178 has commenced, with the wedge sled 180 having distally traversed off of the tines 238 of the lockout arm 226. Accordingly, the first end 228 of the lockout arm 226 is pivotally elevated by the biasing means 240, causing the locking pin 244 to contact the firing bar 66. During the subsequent distal movement of the firing bar 66, the locking pin 244 is continually maintained in sliding contact with the firing bar 66 and traverses a proximal portion thereof, including the contoured portion 248.

In FIG. 8, the firing bar 66 is shown immediately subsequent to its retraction. The locking pin 244 has re-traversed the proximal portion of the firing bar 66 in the opposite direction, terminating with its vertical alignment with the notch 246. Because the wedge sled 180 is no longer present in the unfired position, the second end 230 of the lockout arm 226 is maintained in a depressed position with respect to the firing bar 66, resulting in the engagement of the notch 246 by the locking pin 244, as shown in FIG. 8. The compression of the biasing means 240 resulting from the traversal of the locking pin 244 upwardly over the contoured portion 248 ensures that the notch 246 is engaged by the locking pin 244 with a suitable amount of force. Accordingly, the lockout arm 226 is in the locking position, and distal movement of the firing bar 66 is prevented until the spent staple cartridge 178 is replaced.

Figure 9:
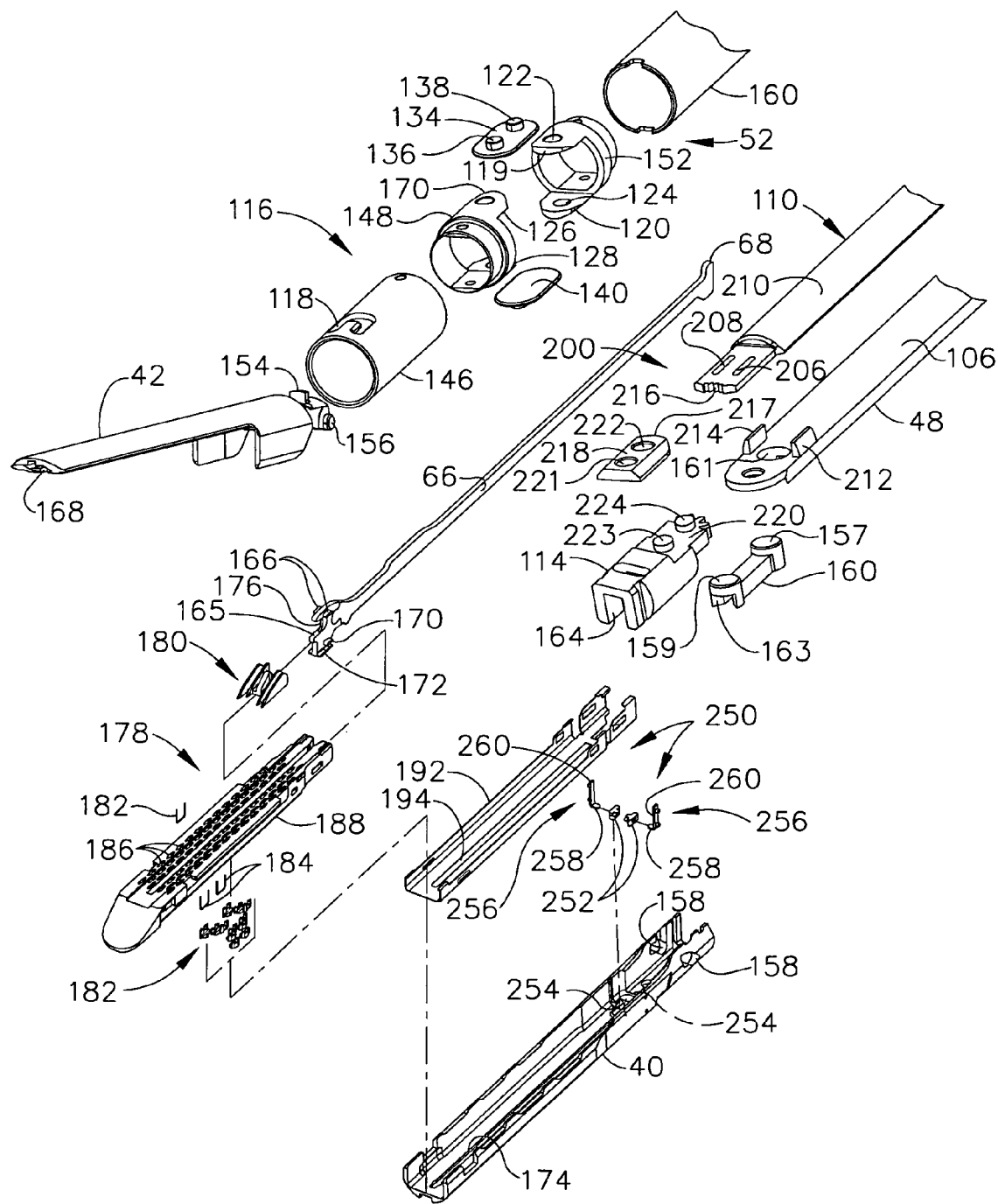
FIG. 9 is a perspective disassembled view of distal portions of an implement portion of the surgical stapling and severing instrument of FIG. 1, including the staple applying assembly and articulation mechanism, according to various embodiments.
Figure 10:
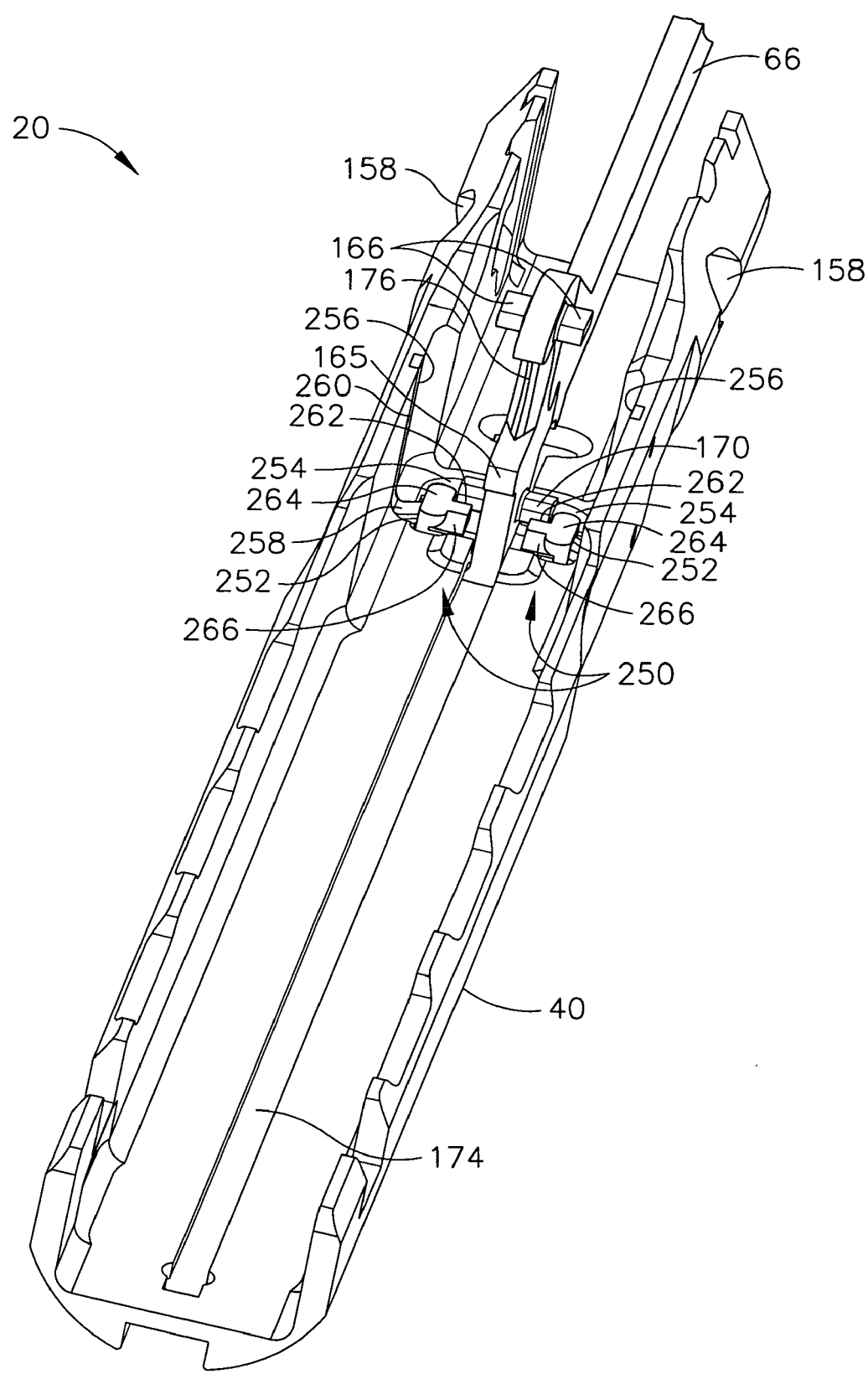
FIG. 10 is a front top perspective view of the end effector of FIG. 9 at the distal end of the surgical stapling and severing instrument, with the staple cartridge and anvil removed, according to various embodiments.

As an alternative to the locking arm 226 of FIGS. 3-4, embodiments of the implement portion 12 of FIG. 9 advantageously incorporate at least one lockout assembly 250 mounted within the elongate channel 40 and adjacently positioned with respect to a corresponding lateral surface of the E-beam 165 when the firing bar 66 is in the retracted position. In preferred embodiments, and as shown in FIG. 9, two lockout assemblies 250 are provided, although it will be appreciated that a single lockout assembly 250 may be utilized instead. Each lockout assembly 250 includes a lockout cartridge 252 movably disposed within a corresponding recess 254 defined by the bottom surface of the elongate channel 40 and configured to move between a locked position and an unlocked position with respect to the E-beam 165 based upon the position of the wedge sled 180. Each lockout assembly 250 further includes biasing means 256 for applying an upwardly-directed force to the lockout cartridge 252 such that a portion of the lockout cartridge 252 is caused to protrude from the corresponding recess 254 when the wedge sled 180 is not present in the unfired position. As shown in FIG. 9, the biasing means 256 for each lockout cartridge 252 may be implemented as a spring finger 256 having an inwardly extending first end 258 attached to the lockout cartridge 252, and an upwardly-extending second end 260 attached to a lateral surface of the elongate channel 40. When in a relaxed (i.e., non-compressed) state, the first end 258 is upwardly inclined such that a portion of the lockout cartridge 252 suitably protrudes from its corresponding recess 254, as best seen in FIG. 10 discussed below. Preferably, the second end 260 of each spring finger 256 is attached in a flush manner (e.g., within a formed recess) to the corresponding elongate channel 40 surface so that the staple cartridge 178 may be accommodated by the elongate channel 40 without modification.

FIG. 10 is a front top perspective view of the assembled end effector 20 of FIG. 9 at the distal end of the surgical stapling and severing instrument 10, with the staple cartridge 178 and anvil 42 removed for the sake of clarity. As shown, each lockout cartridge 252 includes a first proximally-facing lateral surface 262 configured for engaging a corresponding middle pin 170 of the E-beam 165 when the lockout cartridge 252 is in the locked position (i.e., protruding from the recess 254 of the elongate channel 40). Engagement of the middle pins 170 by the lockout cartridges 252 when in the locked position thus prevents distal movement of the firing bar 66.

Each lockout cartridge 252 may further include a second upwardly-facing surface 264 configured for engagement by a bottom surface of the wedge sled 180 when present in the unfired position. Engagement of the second surfaces 264 in this manner is sufficient to overcome the force applied to the lockout cartridges 252 by the biasing means 256. As a result, each lockout cartridge 252 is depressed into its corresponding recess 254 such that the first surface 262 is disengaged from the corresponding middle pin 170 of the E-beam 165, thus enabling distal movement of the firing bar 66. The depressed position of each lockout cartridge 252 corresponds to the locked position thereof.

Each lockout cartridge 252 may further include a third distally-facing inclined surface 266 configured for slidingly engaging the corresponding middle pin 170 of the E-beam 165 immediately prior to the retraction of the firing bar 66. Engagement of the third surface 266 in this fashion operates to momentarily depress each lockout cartridge 252, thus permitting the firing bar 66 to fully retract. Upon full retraction of the firing bar 66, each lockout cartridge 252 is caused to protrude from its corresponding recess 254 in the locked position such that the first surface 262 engages the corresponding middle pin 170. Importantly, because the position of the lock cartridges 252 is based only upon the position of the wedge sled 180, operation of the operation of the lockout assemblies is unaffected by flexure of the firing bar 66 resulting from actuation of the articulation mechanism 14.

Figure 11:
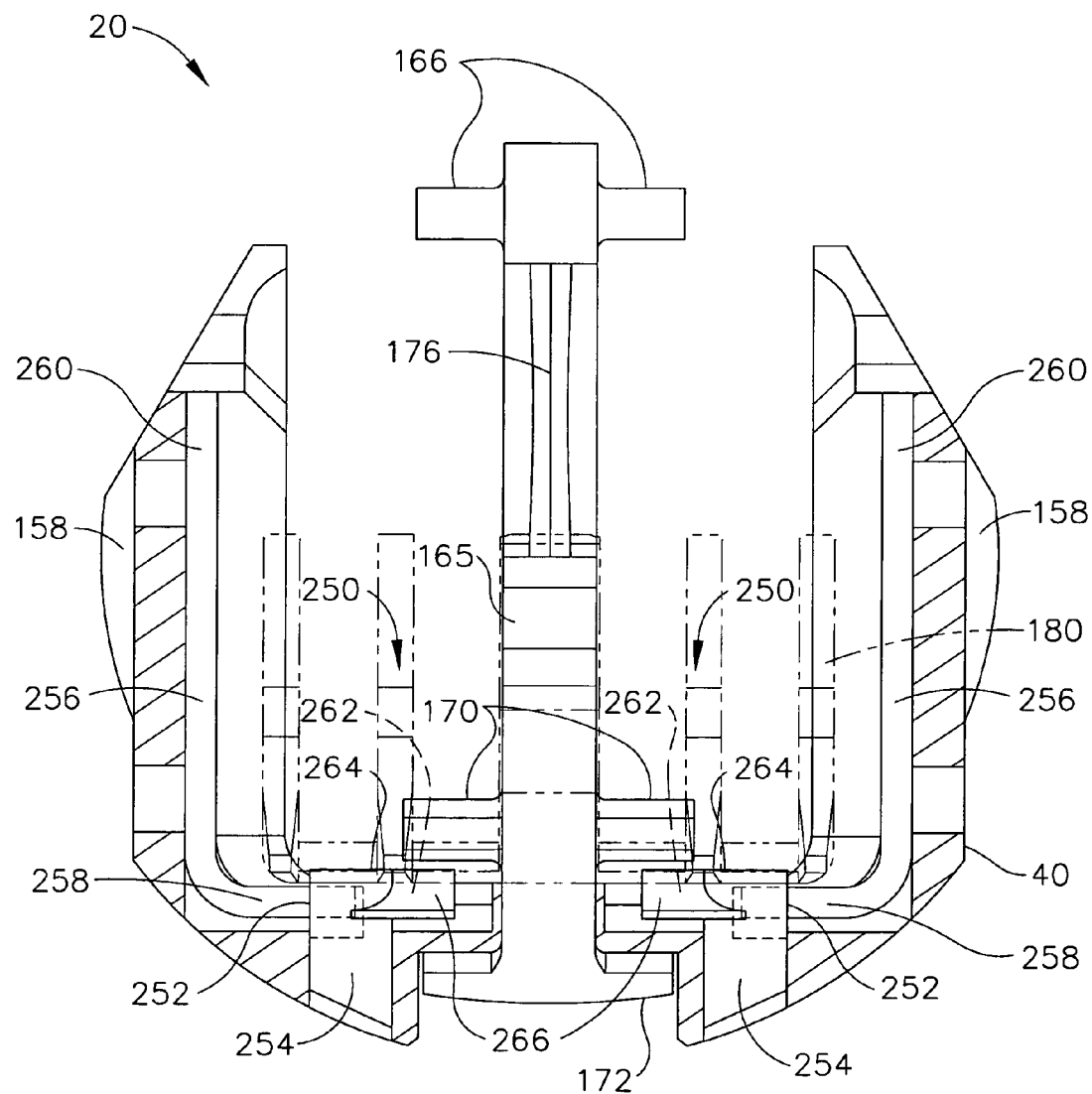
FIGS. 11-13 are cross-sectional front views of the end effector of FIG. 9 sequentially shown in a staple cartridge loaded and unfired state in FIG. 11, a staple cartridge being fired state in FIG. 12, and a spent staple cartridge with firing bar retracted state in FIG. 13, according to various embodiments.
Figure 12:
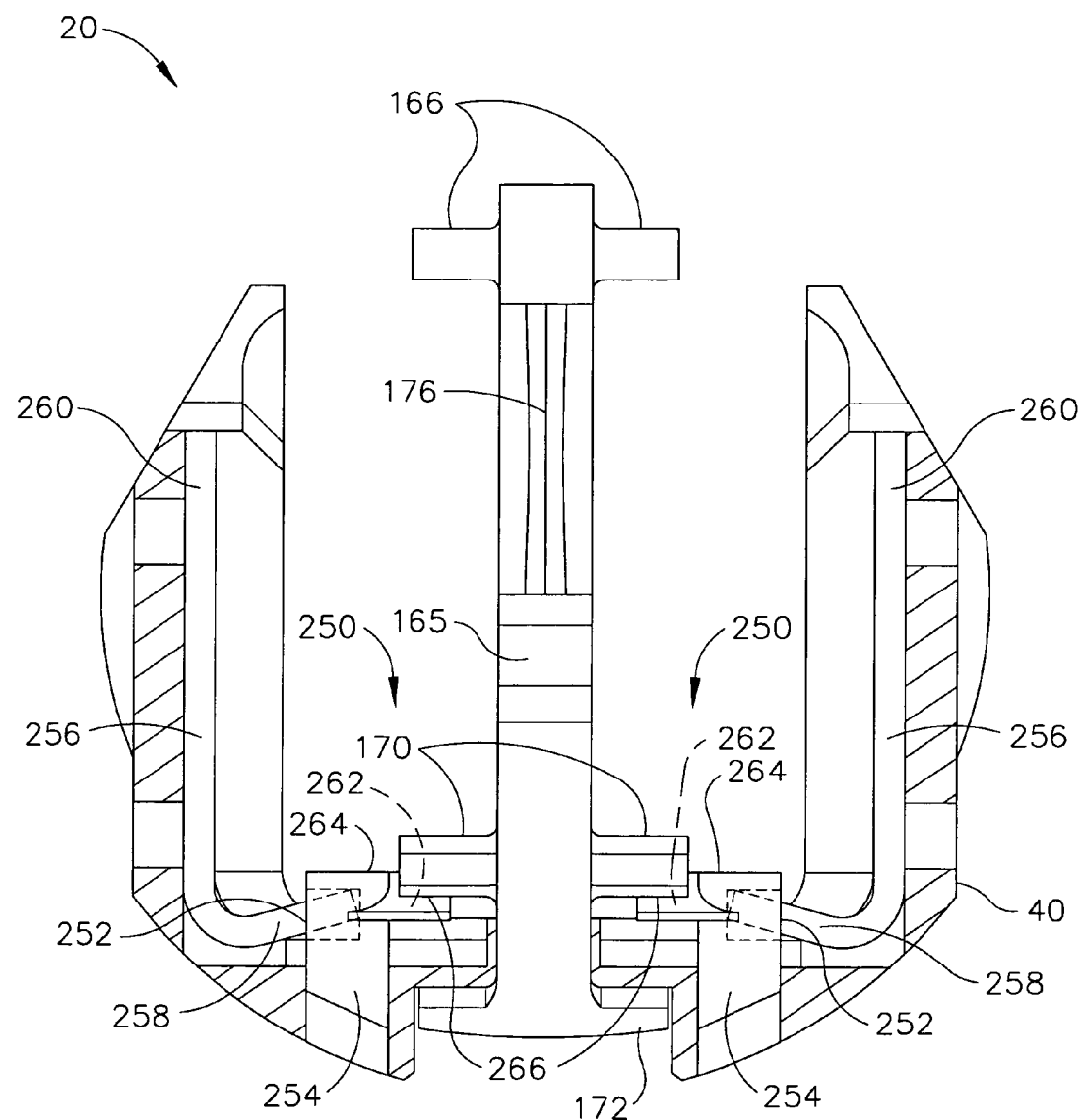
Figure 13:
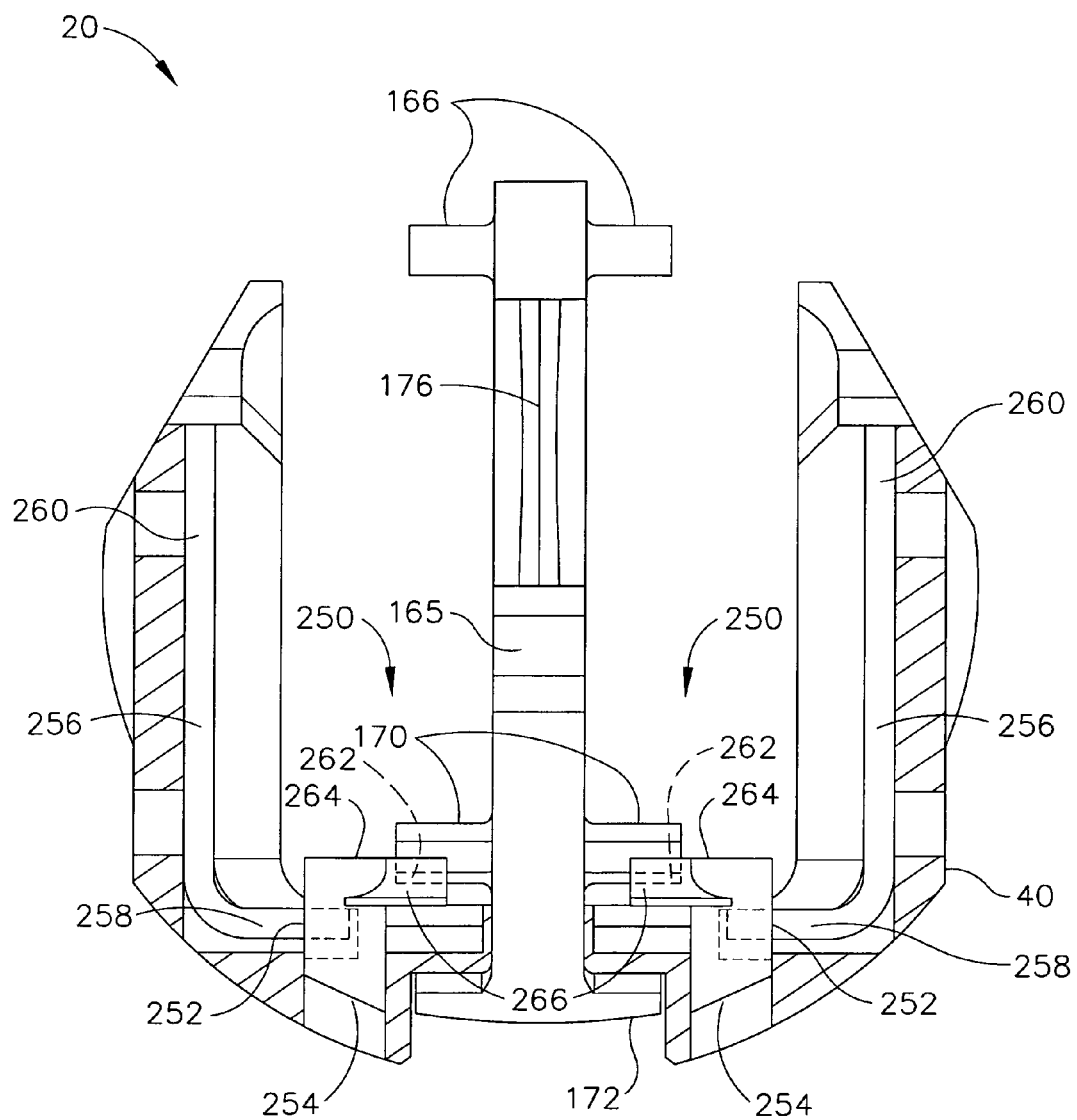

FIGS. 11-13 depict sequential operation of the lockout assemblies 250 within the end effector of FIGS. 9-10 as the surgical stapling and severing instrument 10 is fired. In FIG. 11, an unfired staple cartridge 178 has been inserted into the elongate channel 40, with the wedge sled 180 engaging the second surfaces 264 such that each lockout cartridge 252 is depressed into its corresponding recess 254 within the elongate channel 40. Accordingly, each lockout cartridge 252 is maintained in the unlocked position, and the first surfaces 262 are disengaged from the corresponding middle pins 170 of the E-beam 165.

In FIG. 12, firing of the staple cartridge 178 has commenced, with the wedge sled 180 (not shown) having distally traversed off of the second surfaces 264 of the lockout cartridges 252. Accordingly, the lockout cartridges 252 are caused to protrude from their corresponding recesses 254 as a result of the force applied thereto by the biasing means 256.

In FIG. 13, the E-beam 165 is shown in the fully retracted position subsequent to the sliding engagement of the third surfaces 266 of the lockout cartridges 252 by the corresponding middle pins 170. Because the wedge sled 180 is no longer present in the unfired position, each lockout cartridge 252 protrudes from its corresponding recess 254 in the locked position such the middle pins 170 are engaged by the first surfaces 262, thus preventing subsequent distal movement of the firing bar 66 until the spent staple cartridge 178 is replaced.

Figure 14:
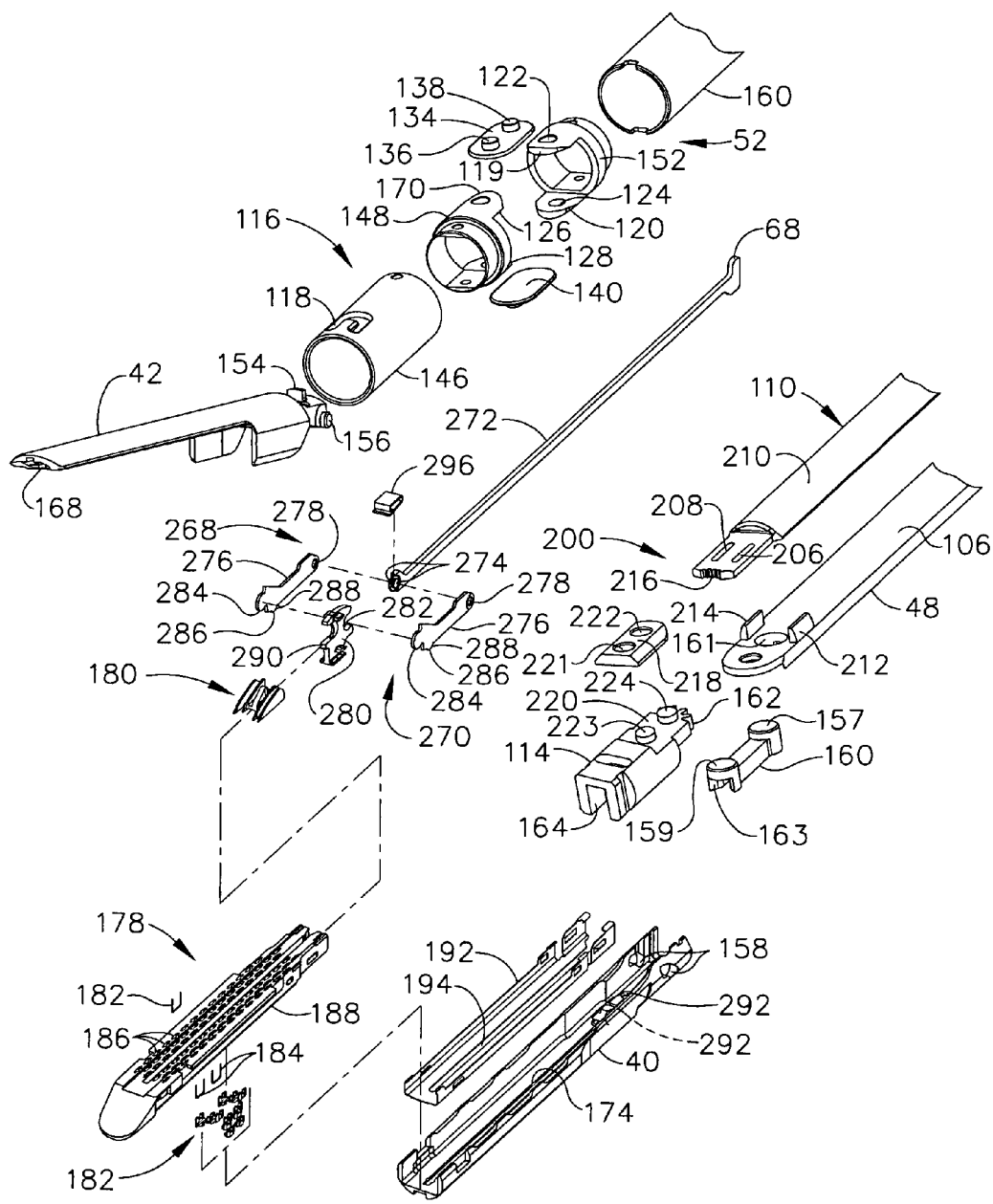
FIG. 14 is a perspective disassembled view of distal portions of an implement portion of the surgical stapling and severing instrument of FIG. 1, including the staple applying assembly and articulation mechanism, according to various embodiments.

As an alternative to the lockout arm 226 of FIGS. 3-4 and the lockout assemblies 250 of FIGS. 9-10, embodiments of the implement portion 12 of FIG. 14 advantageously incorporate a two-piece firing bar 268 including a distal portion 270 pivotally attached to a proximal portion 272. The distal portion 270 of the firing bar 268 is configured to pivot between locked and unlocked positions with respect to the elongate channel 40 based upon a position of the wedge sled 180.

As shown in FIG. 14, the proximal portion 272 includes a pair of pivot pins 274 distally positioned on opposing lateral surfaces thereof. The distal portion 270 includes a pair of symmetrically formed pivot plates 276, each having a proximal hole 278 formed therein for cooperatively engaging a corresponding pivot pin 274 of the proximal portion 272. The distal portion 270 further includes an E-beam 280 similar to the E-beam 165 of described above and having a contoured proximal recess 282 for engaging an oppositely-contoured pin 284 formed by the distal end of each pivot plate 276, thus enabling a generally rigid connection to be formed therebetween. The distal portion 270 of the firing bar 268, including the E-beam 280, is thus permitted to pivot in a vertical plane with respect to the proximal portion 272 thereof.

Each pivot plate 276 further includes a downwardly-extending pin 286 formed on the bottom at distal end thereof and comprising a proximally-facing contoured surface 288. When the pivot plates 276 are engaged by the E-beam 280, the pins 286 are maintained in alignment and thus effectively define a common pin. When the firing bar 268 is in the fully retracted position, the pins 286 contact a bottom portion of the elongate channel 40 adjacent to the proximal end of the longitudinal opening 174, thus supportably maintaining the distal portion 270 in an elevated position with respect to the elongate channel 40. When the firing bar 268 is in a position other than the fully retracted position (e.g., during extension or retraction), the pins 286 are aligned with the longitudinal slot 174 and no longer contact a bottom portion of the elongate channel 40. Thus, for such positions, the distal portion 270 is not supported by the pins 286.

The E-beam 280 includes a nose 290 formed at the distal end thereof configured for supportable engagement by a proximal portion wedge sled 180. Accordingly, during distal movement of the wedge sled 180 resulting from extension of the firing bar 268, the nose 290 maintains the E-beam 280 (and thus the distal portion 270 of the firing bar 268) in an elevated position with respect to the elongate channel 40. The elevated position of the distal portion 270 resulting from supportable engagement of the nose 290 by the wedge sled 180 corresponds to the unlocked position thereof.

Figure 15:
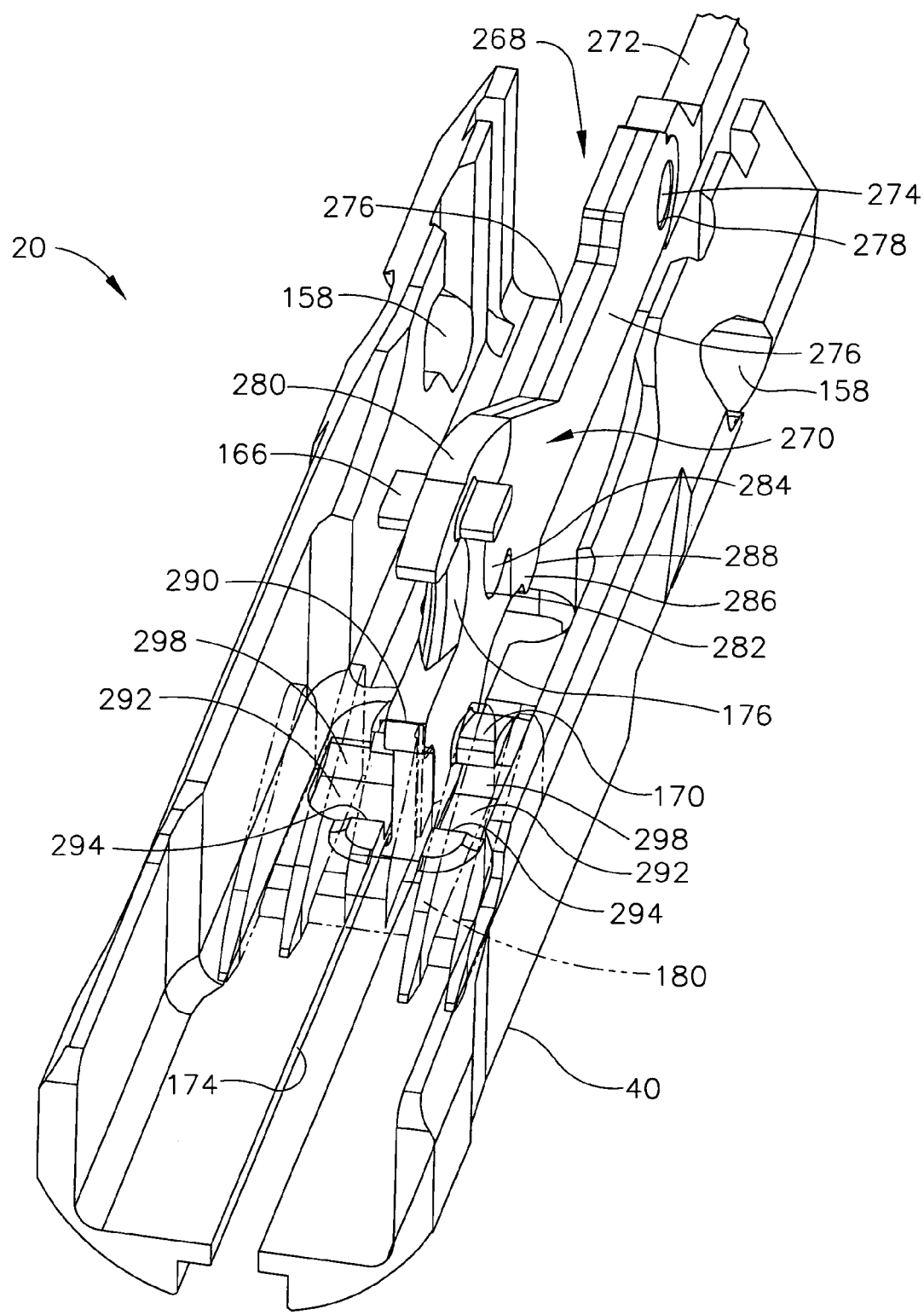
FIG. 15 is a front top perspective view of the end effector of FIG. 14 at the distal end of the surgical stapling and severing instrument, with the anvil removed and only the wedge sled of the staple cartridge shown, according to various embodiments.

As best seen in FIG. 15, the elongate channel 40 includes a pair of recesses 292 defined by a bottom portion thereof and symmetrically disposed on opposing sides of the longitudinal slot 174. The recesses 292 are positioned such that each is located under and slightly forward of a corresponding middle pin 170 of the E-beam 280 when the firing bar 268 is fully retracted. When the wedge sledge sled 180 is not present in the unfired position, the nose 290 of the E-beam 280 is unsupported during extension of the firing bar 268. The distal portion 270 of the firing bar 268 is thus permitted to pivot downward into a depressed position with respect to the elongate channel 40 such that the middle pins 170 are received into the corresponding recesses 292. Each recess 292 defines a vertically-oriented distal surface 294 for engaging an opposing distal portion of the corresponding middle pin 170, thus preventing further distal movement of the firing bar 268. The depressed position of the distal portion 270 thus corresponds to the locked position thereof. As shown in FIG. 14, biasing mean 296, depicted as spring member 296, may be incorporated within the implement portion 12 for downwardly urging the distal portion 270 into the locked position.

Referring again to FIG. 15, each recess 292 further defines a sloped proximal surface 298 for slidingly engaging the corresponding middle pins 170 during retraction of the firing bar 268 such that the distal portion 270 is caused to pivot upward, thus facilitating extraction of the middle pins 170 from the recesses 292. Retraction of the firing bar 268 into the fully retracted position causes the contoured surfaces 288 of the pins 286 to slidingly engage the bottom portion of the elongate channel 40 adjacent to the proximal end of the longitudinal slot 174, thus transitioning the distal portion 270 into the unlocked position.

In FIG. 15, the firing bar 268 is depicted in a fully retracted state, with the distal portion 270 maintained in the pivotally elevated position (i.e., unlocked position) with respect to the elongate channel 40. Importantly, because only the distal portion 270 of the firing bar 268 need be elevated or depressed to transition between the unlocked and locked positions, the locking mechanism is unaffected by any flexure of the proximal portion 272 resulting from actuation of the articulation mechanism 14.

Figure 18:
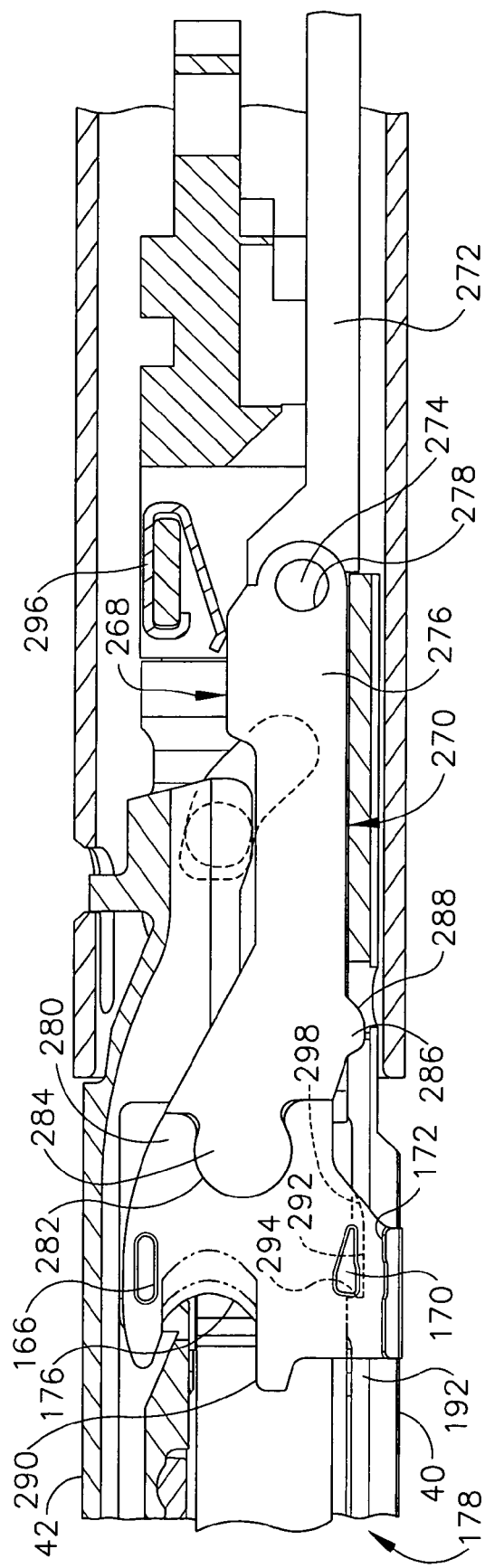

FIGS. 16-18 depict sequential operation of the firing bar 268 within the end effector 20 of FIG. 14 as the surgical stapling and severing instrument 10 is fired. In FIG. 16, an unfired staple cartridge 178 has been inserted into the elongate channel 40, with a proximal portion of the wedge sled 180 supportably engaging the nose 290 of the E-beam 280. The distal portion 270 is supported in the elevated (i.e., unlocked) position by the pins 286, and the middle pins 170 are positioned above the corresponding recesses 292.

In FIG. 17, firing of the staple cartridge 178 has commenced. Although the distal portion 270 is no longer supported by the pins 286, the engagement of the nose 290 by the wedge sled 180 prevents the distal portion 270 from pivoting downward in response to the force applied thereto by the biasing means 296. Thus, the distal portion 270 remains sufficiently elevated such that the middle pins 170 are not received into the recesses 292, permitting continued distal movement of the firing bar 268.

In FIG. 18, firing bar 268 is shown subsequent to being fully retracted and re-fired without replacement of the now-spent staple cartridge 178. Because the wedge sled 180 is no longer present, the nose 290 of the E-beam 280 is not supportingly engaged thereby. The biasing means 296 thus causes the distal portion 270 to be pivotally depressed into the locking position such that the middle pins 170 are received into their corresponding recesses 292. Engagement of the middle pins 170 by the distal surfaces 294 of the recesses 292 prevents further distal movement of the firing bar 268.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, it will be appreciated that embodiments of the above-described locking mechanisms may be incorporated into articulating surgical stapling and severing instruments having articulating mechanisms controllable by means other than a fluidic actuation, such as gear-driven articulation mechanisms. It will further be appreciated that embodiments of the above-described locking mechanisms are not limited in their application to articulating instrument designs and may also be advantageously incorporated within non-articulating instruments.

The invention claimed is:

1. A surgical instrument comprising:
   a handle portion operably configured to produce a firing motion;
   a channel coupled to the handle portion;
   an anvil pivotally attached to the channel;
   a staple cartridge engaged by the channel and including a plurality of staple drivers and staples, the staple drivers for camming the staples toward the anvil;
   a wedge member proximal to and longitudinally aligned with the staple drivers;
   a reciprocating firing device responsive to the firing motion to progressively drive the wedge member from an unfired position to a fired position; and
   a lockout arm pivotally attached to the channel and operably configured to pivot between a locked position and an unlocked position with respect to the firing device based upon a position of the wedge member;
   wherein the lockout arm comprises a first end, a second end, and pivot means located between the first and second ends, the pivot means cooperative with the channel;
   wherein the first end of the lockout arm is operably configured for depressible engagement by the wedge member when present in the unfired position such that the second end of the lockout arm is pivoted in an elevated position with respect to the firing device, the depressed engagement of the first end and the elevation of second end corresponding to the unlocked position of the lockout arm; and a biasing means for applying a force for elevating the first end of the lockout arm such that the second end thereof is pivoted in a depressed position with respect to the firing device when the wedge member is not present in the unfired position, the elevation of the first end and the depression of the second end corresponding to the locked position of the lockout arm;

wherein the second end of the lockout arm is operably configured to engage the firing device when the lockout arm is in the locked position such that distal movement of the firing device is prevented.

2. The surgical instrument of claim 1, further comprising a shaft for connecting the handle portion to the channel, the shaft comprising an articulation mechanism.

3. The surgical instrument of claim 1, wherein the lockout arm defines an open-ended slot passing through the first end and entering a portion of the second end.

4. The surgical instrument of claim 1, wherein the second end of the lockout arm comprises a lock pin for engaging a notch defined by the firing device when the lockout arm is in the locked position.

5. A surgical instrument comprising:
a handle portion operably configured to produce a firing motion;
a channel coupled to the handle portion;
an anvil pivotally attached to the channel;
a staple cartridge engaged by the channel and including a plurality of staple drivers and staples, the staple drivers for camming the staples toward the anvil;
a wedge member proximal to and longitudinally aligned with the staple drivers;
a reciprocating firing device responsive to the firing motion to progressively drive the wedge member from an unfired position to a fired position; and
at least one lockout assembly positioned in the channel and adjacent to a corresponding lateral surface of the firing device, each lockout assembly comprising a lockout cartridge moveably disposed within a corresponding recess defined by the channel, wherein the lockout cartridge is configured to move between a locked position and an unlocked position with respect to the firing device based upon a position of the wedge member;

wherein each lockout assembly further comprises biasing means for applying a force to the lockout cartridge such that a portion of the lockout cartridge is caused to protrude from the corresponding recess when the wedge member is not present in the unfired position, the protrusion of the lockout cartridge from the recess corresponding to the locked position thereof;

wherein the biasing means of each lockout assembly comprises a spring finger having a first end attached to the lockout cartridge and a second end attached to the channel; and wherein the lockout cartridge of each lockout assembly comprises a first surface configured for engaging a corresponding pin of the firing device when the lockout cartridge is in the locked position such that distal movement of the firing device is prevented.

6. The surgical instrument of claim 5, further comprising a shaft for connecting the handle portion to the channel, the shaft comprising an articulation mechanism.

7. The surgical instrument of claim 5, wherein the lockout cartridge of each lockout assembly further comprises a second surface configured for engagement by the wedge member when present in the unfired position such that the lockout cartridge is depressed into the corresponding recess, the depression of the lockout cartridge corresponding to the unlocked position thereof.

8. The surgical instrument of claim 7, wherein the lockout cartridge of each lockout assembly further comprises a third surface configured for slidingly engaging the corresponding pin on the firing device during reciprocating movement thereof.

* * * * *